US009046525B2

(12) United States Patent
Walton et al.

(10) Patent No.: US 9,046,525 B2
(45) Date of Patent: Jun. 2, 2015

(54) METHOD OF DETERMINING THE OLIGOMERIC STATE OF A PROTEIN COMPLEX

(75) Inventors: Troy Walton, Pasadena, CA (US); Chris Gandhi, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 776 days.

(21) Appl. No.: 13/195,788

(22) Filed: Aug. 1, 2011

(65) Prior Publication Data

US 2012/0034619 A1 Feb. 9, 2012

Related U.S. Application Data

(60) Provisional application No. 61/369,601, filed on Jul. 30, 2010.

(51) Int. Cl.
*G01N 33/53* (2006.01)
*C12Q 1/37* (2006.01)
*G01N 33/68* (2006.01)

(52) U.S. Cl.
CPC ........ *G01N 33/6803* (2013.01); *G01N 33/6842* (2013.01); *G01N 2333/95* (2013.01); *G01N 2550/00* (2013.01)

(58) Field of Classification Search
CPC ............ G01N 33/68033; C12N 15/62; C07K 2319/50; C07K 2319/60; C07K 2319/61; C07K 2319/70; C07K 2319/705
See application file for complete search history.

(56) References Cited

U.S. PATENT DOCUMENTS

| 2003/0082522 | A1* | 5/2003 | Haynes et al. | 435/5 |
| 2006/0073485 | A1* | 4/2006 | Schneider et al. | 435/6 |
| 2006/0141554 | A1* | 6/2006 | Gee et al. | 435/40.5 |
| 2006/0154318 | A1* | 7/2006 | Anderson | 435/7.92 |
| 2008/0044857 | A1* | 2/2008 | Anderson | 435/71.1 |
| 2008/0113875 | A1* | 5/2008 | Chaurand et al. | 506/9 |
| 2009/0233806 | A1* | 9/2009 | Carr | 506/9 |
| 2009/0311720 | A1* | 12/2009 | Roos et al. | 435/7.21 |
| 2011/0097737 | A1* | 4/2011 | Samuelson et al. | 435/7.4 |
| 2012/0043208 | A1* | 2/2012 | Jin et al. | 204/452 |
| 2012/0046191 | A1* | 2/2012 | Vu et al. | 506/9 |
| 2013/0203101 | A1* | 8/2013 | Bren et al. | 435/29 |

OTHER PUBLICATIONS

Meyer, E. H., et al., 2008, "Resolving and identifying protein components of plant mitochondrial respiratory complexes using three dimensions of gel electrophoresis", Journal of Proteome Research, vol. 7, No. 2, pp. 786-794.*
Morin, T. J., et al., 2008, "Counting membrane-embedded KCNE β-subunits in functioning K+ channel complexes", Proceedings of the National Academy of Sciences of the USA, vol. 105, No. 5, pp. 1478-1481.*

(Continued)

*Primary Examiner* — Manjunath Rao
*Assistant Examiner* — William W Moore
(74) *Attorney, Agent, or Firm* — Christie, Parker & Hale, LLP

(57) ABSTRACT

A method of counting protein subunits to determine the oligomeric state of an oligomeric protein complex includes tagging and expressing the protein subunits with a mass/charge tag and selectively removing each mass/charge tag. The number of protein subunits of the oligomeric complex corresponds to the number of mass/charge tags removed.

17 Claims, 23 Drawing Sheets

(56) References Cited

OTHER PUBLICATIONS

Kohout, S. C., et al., 2008, "Subunit organization and functional transitions in Ci-VSP", Nature Structural & Molecular Biology, vol. 15, No. 1, pp. 106-108.*

Ding, H., et al., 2009, "Determination of the oligomer size of amyloidogenic protein β-amyloid(1-40) by single molecule spectroscopy", Biophysical Journal, vol. 97, No. 3, pp. 912-921.*

Nakajo, K., et al., 2010, "Stoichiometry of the KCNQ1—KCNE1 ion channel complex", Proceedings of the National Academy of Sciences of the USA, vol. 107, No. 44, pp. 18862-18867.*

Groulx, N., et al., 2011, "Single Molecule Fluorescence Study of the *Bacillus thuringiensis* Toxin Cry1Aa Reveals Tetramerization", The Journal of Biological Chemistry, vol. 286, No. 49, pp. 42274-42282.*
Arnau, Jose et al.; "Current strategies for the use of affinity tags and tag removal for the purification of recombinant proteins"; Protein Expression & Purification; 48; 2006; 1-13.
Bertani, Giuseppe; "Lysogeny at Mid-Twentieth Century:P1, P2, and Other Experimental Systems"; Guest Commentary; Journal of Bacteriology; Feb. 2004; pp. 595-600.
Blount, Paul et al.; "Membrane topology and multimeric structure of a mechanosensitive channel protein of *Escherichia coli*"; The EMBO Journal; vol. 15; No. 18; 1996; pp. 4798-4805.
Chang, Geoffrey et al.; Structure of the MscL Homolog from *Mycobacterium tuberculosis*: A Gated Mechanosensitive Ion Channel; Science 282; 1998; pp. 2220-2226.
Cordingley, Michael G. et al.; "Substrate Requirements of Human Rhinovirus 3C Protease for Peptide Cleavage in Vitro"; The Journal of Biological Chemistry; vol. 265; Jun. 5, 1990; pp. 9062-9065.
Friezner Degen, Sandra J. et al.,; "Nucleotide Sequence of the Gene for Human Prothrombin"; Biochemistry; vol. 26; 1987; pp. 6165-6177.
Folgering, Joost H.A. et al.; "Engineering covalent oligomers of the mechanosensitive channel of large conductance from *Escherichia coli* with native conductance and gating characteristics"; Protein Science; 2005; vol. 14; pp. 2947-2954.
Friedman, David B. et al.; "Isoelectric Focusing and Two-Dimensional Gel Electrophoresis"; Methods in Enzymology; Chapter 30; vol. 463; 2009; pp. 515-540.
Gandhi, Chris S. et al.; "OCAM: A new tool for studying the oligomeric diversity of MscL channels"; Protein Science 2011; vol. 20; pp. 313-326.
Gianazza, Elisabetta et al.; "Immobilized pH gradients"; Electrophoresis 2009; Vol, 30; pp. S112-S121.
Huang, Lei et al, "Functional Expression and Purification of Bovine Enterokinase Light Chain in Recombinant *Escherichia coli*"; Preparative Biochemistry & Biotechnology; vol. 37; 2007; pp. 205-217.
Klock, Heath E. et al.; "Combining the polymerase incomplete primer extension method for cloning and mutagenesis with microscreening to accelerate structural genomics efforts"; Proteins 2008; vol. 71; pp. 982-994.
Liu, Zhenfeng et al.; "Structure of a tetrameric MscL in an expanded intermediate state"; Nature; vol. 461; Sep. 3, 2009; pp. 120-124.
Ma, Jichun et al.; "The use of blue native PAGE In the evaluation of membrane protein aggregation states for crystallization"; Journal of Applied Crystallography; 2008; vol. 41; pp. 1150-1160.
Messier, Terri L. et al.; Cloning and expression in COS-1 cells of a full-length cDNA encoding human coagulation factor X (Recombinant DNA; blood clotting; vitamin K; prothrombin activation; serine protease); Gene. 99; 1991; pp. 291-294.
Moe, Paul C. et al.; "Conelating a Protein Strttettire with Function of a Bacterial Mechanosensitive Channel"; The Journal of Biological Chemistry; Oct. 6, 2000; vol. 275; No. 40; pp. 31121-31127.
Mohanty, Arun K. et al.; "Inhibition of tobacco etch virus protease activity by detergents"; Protein Expression and Purification; vol. 27; 2003; pp. 109-114.
Pedelacq, Jean-Denis et al.; "Engineering and characterization of a superfolder green fluorescent protein"; Nature biotechnology; vol. 24; No. 1; Jan. 2006; pp. 79-88.
Qiagen; The QIAexpressionist; "A handbook for high-level expression and purification of 6xHis-tagged proteins"; Jun. 2003; Fifth Edition; 128pp.
Saint, Nathalie et al.; "A Hexameric Transmembrane Pore Revealed by Two-dimensional Crystallization of the Large Mechanosensitive Ion Channel (MscL) of *Escherichia coli*"; The Journal of Biological Chemistry; Communication; vol. 273; No. 24; Jun. 12, 1998; pp. 14667-14670.
Schagger, Hermann et al,; "Analysis of Molecular Masses and Oligomeric States of Protein Complexes by Blue Native Electrophoresis and Isolation of Membrane Protein Complexes by Two-Dimensional Native Electrophoresis"; Analytical Biochemistry; vol. 217; 1994; pp. 220-230.
Schwarz, Daniel et al.; "Preparative scale cell-free expression systems: New tools for the large scale preparation of integral membrane proteins for functional and structural studies"; ScienceDirect: Methods 41; 2007; pp. 355-369.
Sleight, Sean C, et al.; "In-Fusion BioBrick assembly and re-engineering"; Nucleic Acids Research; 2010; vol. 38; No, 8; pp. 2624-2636.
Smith, Caitlin; "Keeping tabs on fluorescent tags"; Technology Feature; Nature Methods; vol. 4; No. 9; Sep. 2007; pp. 755-761.
Sommer, Greg J. et al.; "IEF in microfluidic devices"; Review; Electrophoresis 2009; vol. 30; pp. 742-757.
Steinbacher, Stefan et al.; "Structures of the Prokaryotic Mechanosensitive Channels MscL and MscS"; Chapter 1; Current Topics in Membranes; vol. 58; 2007; pp. 1-24.
Stenberg, Flippa et al.; "Protein Complexes of the *Escherichia coli* Cell Envelope"; Journal of Biological Chemistry; vol. 280; No. 41; Oct. 14, 2005; pp. 34409-34419.
Sijkharev, Sergei I. et al.; "A large-conductance mechanosensitive channel in *E. coli* encoded by mscL alone"; Letters to Nature; vol. 368; Mar. 17, 1994; pp. 265-268.
Sukharev, Sergei I. et al.; "Stoichiometry of the Large Conductance Bacterial Mechanosensitive Channel of *E. coli.* A Biochemical Study"; The Journal of Membrane Biology; vol. 171; 1999; pp. 183-193.
Wittig, Ilka et al.; "Blue native PAGE"; Nature Protocols; vol. 1; No. 1; 2006; pp. 418-428.
Yoshimura, Kenbro et al.; "Gating-associated conformational changes in the mechanosensitive channel MscL"; PNAS; Physiology; vol. 105; No. 10; Mar. 11, 2008; pp. 4033-4038.
Zilberstein, Gleb et al.; "Third generation of focusing: Gel matrices with immobilized cation gradients"; Review; Electrophoresis 2010; vol. 31; pp. 1747-1753.

* cited by examiner

Detergent compatibility of SaMscL(CΔ26)

|  | DM | DDM | FC12 | OG | LDAO | C12E8 |
|---|---|---|---|---|---|---|
| Solubility | ++ | ++ | ++ | + | ++ | ++ |
| BN PAGE | ++ | ++ | ++ | ++ | - | ++ |
| TEV digestion | ++ | ++ | + | - | nd | ++ |

FIG. 5

| | | | | | |
|---|---|---|---|---|---|
| SEQ ID NO: 4 | MtMscL-sGFP | | | | |
| SEQ ID NO: 5 | SaMscL-sGFP | | | | |
| SEQ ID NO: 6 | EcMscL-sGFP | | | | |

```
                        10              20              30              40              50
MtMscL-sGFP    M G H H H H H H H H H H S S G H I D D D D K H M - - L K G F - K E F L A R G N I V   D L A V V V I G T
SaMscL-sGFP    M G - - S S H H H H H H H H S S G L V P R G S H - M - - L K E F - K E F A L K G N V L   D L A I A V V M G A
EcMscL-sGFP                                                   M S I - I K E F - R E F A M R G N V V   D L A V G V I I G A 60              70              80              90              100
MtMscL-sGFP    A F T A L V T K F F T D S I - - I T P L I N R I - - G V N A Q S D - - V G I L R I G I G - - G G Q T I D L N V
SaMscL-sGFP    A F N K I - S S L V E N I - - M P L L I G K I - F G S V D F A K E - - W - - - - - - - - - S F W G I K Y G L
EcMscL-sGFP    A F G K I V S S L V A D I - - I M P P L G L L I G G I D F K Q F - - A V T L R D A G G D   I P A V V M H Y G V 110             120             130             140             150
MtMscL-sGFP    L L S A A I N F F L - I A F A V Y Y F L V V - L P Y N T L R K - K - G E V E Q - P G D T - - Q V V L L T E I R
SaMscL-sGFP    F I Q S V I D F L I - - A F A L F I F V K V - I A - - N T L M K K - - E E A E E E A V V E   E N V V L L T E I R
EcMscL-sGFP    F I Q N V F D F L I - - V A F A I F M A I K L - - N K L N R R K K   E E P A A A P A P T   K E E V L L T E I R 160             170             180             190             200
MtMscL-sGFP    D L L A Q T N G D S P G R H G G R G T P S P T D G P R A S T - - - E S Q
SaMscL-sGFP    D L L R E K K - - - - - - - - - - - - - - - - - - - - - - - - - - - - S A S G E N L   Y F Q | S L S K G E E
EcMscL-sGFP    D L L K E Q N N R S                                                              TEV cleavage site 210             220             230             240             250
               L F T G V V P I L V E L D G D V N G H K F S V R G E G E G D A T N G K L T L K F   I C T T G K L P V P 260             270             280             290             300
               W P T L V T T L T Y G V Q C F S R Y P D H M K Q H D F F K S A M P E G Y V Q E R   T I S F K D D G T Y 310             320             330             340             350
               K T R A E V K F E G D T L V N R I E L K G I D F K E D G N I L G H K L E Y N F N   S H N V Y I T A D K 360             370             380             390             400
               Q K N G I K A N F K I R H N V E D G S V Q L A D H Y Q Q N T P I G D G P V L L P   D N H Y L S T Q S V 410             420             430
               L S K D P N E K R D H M V L L E F V T A A G I T H G M D E L   Y K
```

FIG. 6A

| Number of uncleaved sGFPs | MtMscL (5mer) | MtMscl(CΔ49) (5mer) |
|---|---|---|
| 5 | 233.5 | 208.1 |
| 4 | 206.6 | 181.2 |
| 3 | 179.8 | 154.4 |
| 2 | 153.0 | 127.6 |
| 1 | 126.2 | 100.8 |
| 0 | 99.3 | 74.0 |

FIG. 6B

| Number of uncleaved sGFPs | Sa (5mer) | SaMscL(CΔ26) (5mer) | (4mer) |
|---|---|---|---|
| 5 | 218.4 | 203.2 | |
| 4 | 191.6 | 176.4 (13.8) | 162.6 |
| 3 | 164.8 | 149.6 (13) | 135.8 |
| 2 | 138.0 | 122.8 | 109.0 |
| 1 | 111.2 | 96.0 | 82.2 |
| 0 | 84.4 | 69.2 | 55.4 |

FIG. 6C

| Number of uncleaved sGFPs | (6mer) | EcMscL (5mer) | (4mer) |
|---|---|---|---|
| 6 | 270.1 | | |
| 5 | 243.3 (18.2) | 225.1 | |
| 4 | 216.5 (8.6) | 198.3 (18.2) | 180.1 |
| 3 | 189.7 | 171.5 (8.6) | 153.3 |
| 2 | 162.9 | 144.7 | 126.5 |
| 1 | 136.1 | 117.9 | 99.7 |
| 0 | 109.3 | 91.1 | 72.9 |

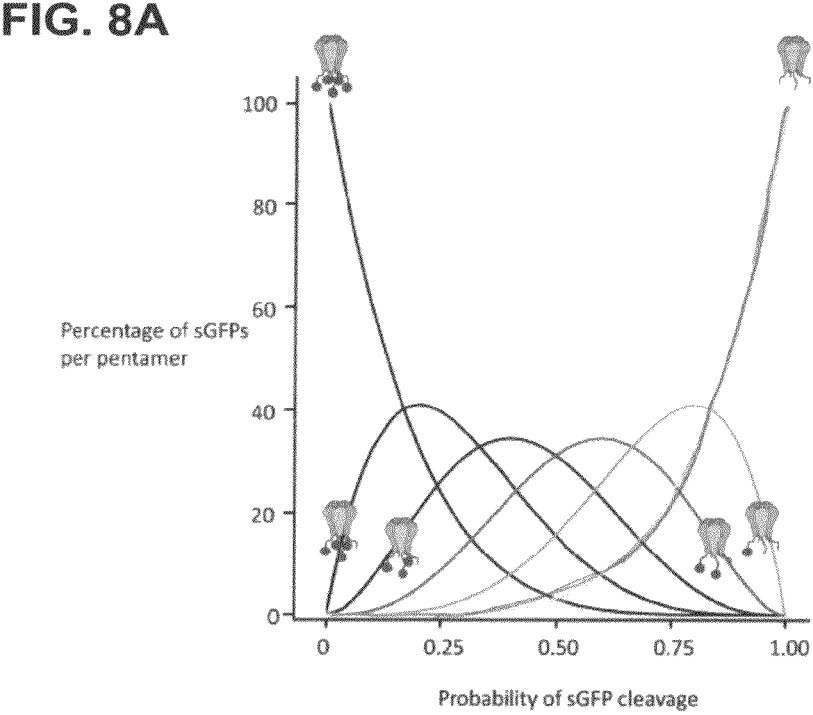

SEQUENCE LISTING

<160> NUMBER OF SEQ ID NOS: 6

<210> SEQ ID NO 1
<211> LENGTH: 151
<212> TYPE: PRT
<213> ORGANISM: Mycobacterium tuberculosis

<400> SEQUENCE: 1

```
Met Leu Lys Gly Phe Lys Glu Phe Leu Ala Arg Gly Asn Ile Val Asp
1               5                   10                  15

Leu Ala Val Ala Val Val Ile Gly Thr Ala Phe Thr Ala Leu Val Thr
                20                  25                  30

Lys Phe Thr Asp Ser Ile Ile Thr Pro Leu Ile Asn Arg Ile Gly Val
            35                  40                  45

Asn Ala Gln Ser Asp Val Gly Ile Leu Arg Ile Gly Ile Gly Gly Gly
        50                  55                  60

Gln Thr Ile Asp Leu Asn Val Leu Leu Ser Ala Ala Ile Asn Phe Phe
65                  70                  75                  80

Leu Ile Ala Phe Ala Val Tyr Phe Leu Val Val Leu Pro Tyr Asn Thr
                85                  90                  95

Leu Arg Lys Lys Gly Glu Val Glu Gln Pro Gly Asp Thr Gln Val Val
            100                 105                 110

Leu Leu Thr Glu Ile Arg Asp Leu Leu Ala Gln Thr Asn Gly Asp Ser
        115                 120                 125

Pro Gly Arg His Gly Arg Gly Thr Pro Ser Pro Thr Asp Gly Pro
    130                 135                 140

Arg Ala Ser Thr Glu Ser Gln
145                 150
```

<210> SEQ ID NO 2
<211> LENGTH: 120
<212> TYPE: PRT
<213> ORGANISM: Staphylococcus aureus

<400> SEQUENCE: 2

```
Met Leu Lys Glu Phe Lys Glu Phe Ala Leu Lys Gly Asn Val Leu Asp
1               5                   10                  15

Leu Ala Ile Ala Val Val Met Gly Ala Ala Phe Asn Lys Ile Ile Ser
                20                  25                  30

Ser Leu Val Glu Asn Ile Ile Met Pro Leu Ile Gly Lys Ile Phe Gly
            35                  40                  45

Ser Val Asp Phe Ala Lys Glu Trp Ser Phe Trp Gly Ile Lys Tyr Gly
        50                  55                  60

Leu Phe Ile Gln Ser Val Ile Asp Phe Ile Ile Ala Phe Ala Leu
65                  70                  75                  80

Phe Ile Phe Val Lys Ile Ala Asn Thr Leu Met Lys Lys Glu Glu Ala
                85                  90                  95

Glu Glu Glu Ala Val Val Glu Glu Asn Val Val Leu Leu Thr Glu Ile
            100                 105                 110

Arg Asp Leu Leu Arg Glu Lys Lys
        115                 120
```

<210> SEQ ID NO 3
<211> LENGTH: 136
<212> TYPE: PRT
<213> ORGANISM: Escherichia coli

<400> SEQUENCE: 3

Met Ser Ile Ile Lys Glu Phe Arg Glu Phe Ala Met Arg Gly Asn Val
1               5                   10                  15

Val Asp Leu Ala Val Gly Val Ile Ile Gly Ala Ala Phe Gly Lys Ile
            20                  25                  30

Val Ser Ser Leu Val Ala Asp Ile Ile Met Pro Pro Leu Gly Leu Leu
        35                  40                  45

Ile Gly Gly Ile Asp Phe Lys Gln Phe Ala Val Thr Leu Arg Asp Ala
    50                  55                  60

Gln Gly Asp Ile Pro Ala Val Val Met His Tyr Gly Val Phe Ile Gln
65                  70                  75                  80

Asn Val Phe Asp Phe Leu Ile Val Ala Phe Ala Ile Phe Met Ala Ile
            85                  90                  95

Lys Leu Ile Asn Lys Leu Asn Arg Lys Lys Glu Glu Pro Ala Ala Ala
            100                 105                 110

Pro Ala Pro Thr Lys Glu Glu Val Leu Leu Thr Glu Ile Arg Asp Leu
            115                 120                 125

Leu Lys Glu Gln Asn Asn Arg Ser
    130                 135

<210> SEQ ID NO 4
<211> LENGTH: 422
<212> TYPE: PRT
<213> ORGANISM: Artificial Sequence
<220> FEATURE:
<223> OTHER INFORMATION: HIS-MtMscL-TEV-GFP

<400> SEQUENCE: 4

Met Gly His His His His His His His His Ser Ser Gly His
1               5                   10                  15

Ile Asp Asp Asp Asp Lys His Met Leu Lys Gly Phe Lys Glu Phe Leu
            20                  25                  30

Ala Arg Gly Asn Ile Val Asp Leu Ala Val Ala Val Val Ile Gly Thr
            35                  40                  45

Ala Phe Thr Ala Leu Val Thr Lys Phe Thr Asp Ser Ile Ile Thr Pro
    50                  55                  60

Leu Ile Asn Arg Ile Gly Val Asn Ala Gln Ser Asp Val Gly Ile Leu
65                  70                  75                  80

Arg Ile Gly Ile Gly Gly Gly Gln Thr Ile Asp Leu Asn Val Leu Leu
            85                  90                  95

Ser Ala Ala Ile Asn Phe Phe Leu Ile Ala Phe Ala Val Tyr Phe Leu
            100                 105                 110

Val Val Leu Pro Tyr Asn Thr Leu Arg Lys Lys Gly Glu Val Glu Gln
            115                 120                 125

Pro Gly Asp Thr Gln Val Leu Leu Thr Glu Ile Arg Asp Leu Leu
            130                 135                 140

Ala Gln Thr Asn Gly Asp Ser Pro Gly Arg His Gly Arg Gly Thr
145                 150                 155                 160

Pro Ser Pro Thr Asp Gly Pro Arg Ala Ser Thr Glu Ser Gln Ser Ala
            165                 170                 175

Ser Gly Glu Asn Leu Tyr Phe Gln Ser Leu Ser Lys Gly Glu Glu Leu
            180                 185                 190

Phe Thr Gly Val Val Pro Ile Leu Val Glu Leu Asp Gly Asp Val Asn
            195                 200                 205

Gly His Lys Phe Ser Val Arg Gly Glu Gly Glu Gly Asp Ala Thr Asn
210                 215                 220

```
Gly Lys Leu Thr Leu Lys Phe Ile Cys Thr Thr Gly Lys Leu Pro Val
225                 230                 235                 240

Pro Pro Thr Leu Val Thr Thr Leu Thr Tyr Gly Val Gln Cys Phe Ser
                245                 250                 255

Arg Tyr Pro Asp His Met Lys Gln His Asp Phe Phe Lys Ser Ala Met
            260                 265                 270

Pro Glu Gly Tyr Val Gln Glu Arg Thr Ile Ser Phe Lys Asp Asp Gly
        275                 280                 285

Thr Tyr Lys Thr Arg Ala Glu Val Lys Phe Glu Gly Asp Thr Leu Val
    290                 295                 300

Asn Arg Ile Glu Leu Lys Gly Ile Asp Phe Lys Glu Asp Gly Asn Ile
305                 310                 315                 320

Leu Gly His Lys Leu Glu Tyr Asn Phe Asn Ser His Asn Val Tyr Ile
                325                 330                 335

Thr Ala Asp Lys Gln Lys Asn Gly Ile Lys Ala Asn Phe Lys Ile Arg
            340                 345                 350

His Asn Val Glu Asp Gly Ser Val Gln Leu Ala Asp His Tyr Gln Gln
        355                 360                 365

Asn Thr Pro Ile Gly Asp Gly Pro Val Leu Leu Pro Asp Asn His Tyr
    370                 375                 380

Leu Ser Thr Gln Ser Val Leu Ser Lys Asp Pro Asn Glu Lys Arg Asp
385                 390                 395                 400

His Met Val Leu Leu Glu Phe Val Thr Ala Ala Gly Ile Thr His Gly
                405                 410                 415

Met Asp Glu Leu Tyr Lys
            420

<210> SEQ ID NO 5
<211> LENGTH: 388
<212> TYPE: PRT
<213> ORGANISM: Artificial Sequence
<220> FEATURE:
<223> OTHER INFORMATION: HIS-SaMscL-TEV-GFP

<400> SEQUENCE: 5

Met Gly Ser Ser His His His His His His Ser Ser Gly Leu Val Pro
1               5                   10                  15

Arg Gly Ser His Met Leu Lys Glu Phe Lys Glu Phe Ala Leu Lys Gly
            20                  25                  30

Asn Val Leu Asp Leu Ala Ile Ala Val Met Gly Ala Ala Phe Asn
        35                  40                  45

Lys Ile Ile Ser Ser Leu Val Glu Asn Ile Ile Met Pro Leu Ile Gly
    50                  55                  60

Lys Ile Phe Gly Ser Val Asp Phe Ala Lys Glu Trp Ser Phe Trp Gly
65                  70                  75                  80

Ile Lys Tyr Gly Leu Phe Ile Gln Ser Val Ile Asp Phe Ile Ile Ile
                85                  90                  95

Ala Phe Ala Leu Phe Ile Phe Val Lys Ile Ala Asn Thr Leu Met Lys
            100                 105                 110

Lys Glu Glu Ala Glu Glu Ala Val Val Glu Asn Val Val Leu
        115                 120                 125

Leu Thr Glu Ile Arg Asp Leu Leu Arg Glu Lys Lys Ser Ala Ser Gly
    130                 135                 140

Glu Asn Leu Tyr Phe Gln Ser Leu Ser Lys Gly Glu Glu Leu Phe Thr
145                 150                 155                 160
```

```
Gly Val Val Pro Ile Leu Val Glu Leu Asp Gly Asp Val Asn Gly His
            165                 170                 175

Lys Phe Ser Val Arg Gly Glu Gly Glu Gly Asp Ala Thr Asn Gly Lys
            180                 185                 190

Leu Thr Leu Lys Phe Ile Cys Thr Thr Gly Lys Leu Pro Val Pro Pro
            195                 200                 205

Thr Leu Val Thr Thr Leu Thr Tyr Gly Val Gln Cys Phe Ser Arg Tyr
210                 215                 220

Pro Asp His Met Lys Gln His Asp Phe Phe Lys Ser Ala Met Pro Glu
225                 230                 235                 240

Gly Tyr Val Gln Glu Arg Thr Ile Ser Phe Lys Asp Asp Gly Thr Tyr
            245                 250                 255

Lys Thr Arg Ala Glu Val Lys Phe Glu Gly Asp Thr Leu Val Asn Arg
            260                 265                 270

Ile Glu Leu Lys Gly Ile Asp Phe Lys Glu Asp Gly Asn Ile Leu Gly
            275                 280                 285

His Lys Leu Glu Tyr Asn Phe Asn Ser His Asn Val Tyr Ile Thr Ala
            290                 295                 300

Asp Lys Gln Lys Asn Gly Ile Lys Ala Asn Phe Lys Ile Arg His Asn
305                 310                 315                 320

Val Glu Asp Gly Ser Val Gln Leu Ala Asp His Tyr Gln Gln Asn Thr
            325                 330                 335

Pro Ile Gly Asp Gly Pro Val Leu Leu Pro Asp Asn His Tyr Leu Ser
            340                 345                 350

Thr Gln Ser Val Leu Ser Lys Asp Pro Asn Glu Lys Arg Asp His Met
            355                 360                 365

Val Leu Leu Glu Phe Val Thr Ala Ala Gly Ile Thr His Gly Met Asp
            370                 375                 380

Glu Leu Tyr Lys
385

<210> SEQ ID NO 6
<211> LENGTH: 404
<212> TYPE: PRT
<213> ORGANISM: Artificial Sequence
<220> FEATURE:
<223> OTHER INFORMATION: HIS-EcMscL-TEV-GFP

<400> SEQUENCE: 6

Met Gly Ser Ser His His His His His His Ser Ser Gly Leu Val Pro
1               5                   10                  15

Arg Gly Ser His Met Ser Ile Ile Lys Glu Phe Arg Glu Phe Ala Met
            20                  25                  30

Arg Gly Asn Val Val Asp Leu Ala Val Gly Val Ile Ile Gly Ala Ala
            35                  40                  45

Phe Gly Lys Ile Val Ser Ser Leu Val Ala Asp Ile Ile Met Pro Pro
            50                  55                  60

Leu Gly Leu Leu Ile Gly Gly Ile Asp Phe Lys Gln Phe Ala Val Thr
65                  70                  75                  80

Leu Arg Asp Ala Gln Gly Asp Ile Pro Ala Val Met His Tyr Gly
            85                  90                  95

Val Phe Ile Gln Asn Val Phe Asp Phe Leu Ile Val Ala Phe Ala Ile
            100                 105                 110

Phe Met Ala Ile Lys Leu Ile Asn Lys Leu Asn Arg Lys Lys Glu Glu
            115                 120                 125
```

-continued

```
Pro Ala Ala Ala Pro Ala Pro Thr Lys Glu Glu Val Leu Leu Thr Glu
    130             135                 140
Ile Arg Asp Leu Leu Lys Glu Gln Asn Asn Arg Ser Ser Ala Ser Gly
145                 150                 155                 160
Glu Asn Leu Tyr Phe Gln Ser Leu Ser Lys Gly Glu Glu Leu Phe Thr
                165                 170                 175
Gly Val Val Pro Ile Leu Val Glu Leu Asp Gly Asp Val Asn Gly His
                180                 185                 190
Lys Phe Ser Val Arg Gly Glu Gly Glu Gly Asp Ala Thr Asn Gly Lys
            195                 200                 205
Leu Thr Leu Lys Phe Ile Cys Thr Thr Gly Lys Leu Pro Val Pro Pro
        210                 215                 220
Thr Leu Val Thr Thr Leu Thr Tyr Gly Val Gln Cys Phe Ser Arg Tyr
225                 230                 235                 240
Pro Asp His Met Lys Gln His Asp Phe Phe Lys Ser Ala Met Pro Glu
                245                 250                 255
Gly Tyr Val Gln Glu Arg Thr Ile Ser Phe Lys Asp Asp Gly Thr Tyr
                260                 265                 270
Lys Thr Arg Ala Glu Val Lys Phe Glu Gly Asp Thr Leu Val Asn Arg
            275                 280                 285
Ile Glu Leu Lys Gly Ile Asp Phe Lys Glu Asp Gly Asn Ile Leu Gly
        290                 295                 300
His Lys Leu Glu Tyr Asn Phe Asn Ser His Asn Val Tyr Ile Thr Ala
305                 310                 315                 320
Asp Lys Gln Lys Asn Gly Ile Lys Ala Asn Phe Lys Ile Arg His Asn
                325                 330                 335
Val Glu Asp Gly Ser Val Gln Leu Ala Asp His Tyr Gln Gln Asn Thr
            340                 345                 350
Pro Ile Gly Asp Gly Pro Val Leu Leu Pro Asp Asn His Tyr Leu Ser
        355                 360                 365
Thr Gln Ser Val Leu Ser Lys Asp Pro Asn Glu Lys Arg Asp His Met
    370                 375                 380
Val Leu Leu Glu Phe Val Thr Ala Ala Gly Ile Thr His Gly Met Asp
385                 390                 395                 400
Glu Leu Tyr Lys
```

METHOD OF DETERMINING THE OLIGOMERIC STATE OF A PROTEIN COMPLEX

CROSS-REFERENCE TO RELATED APPLICATION(S)

The present application claims priority to and the benefit of U.S. Provisional Application Ser. No. 61/369,601 filed on Jul. 30, 2010, the entire contents of which are incorporated herein by reference.

STATEMENT REGARDING FEDERALLY SPONSORED RESEARCH OR DEVELOPMENT

This invention was made with government support under GM084211 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Oct. 7, 2014, is named SEQLISTING13195788.txt and is 14,651 bytes in size.

TECHNICAL FIELD

This application is directed to methods of counting protein subunits in an oligomeric complex.

TECHNICAL BACKGROUND

Quantitation of the number of subunits in an oligomeric protein can be challenging, particularly if multiple forms are present. It is not uncommon for the oligomeric state to be determined for one member of a protein family and then assigned to other members without direct verification. This situation reflects the experimental difficulties associated with unambiguous quantitation of the number of subunits in an oligomer, particularly if multiple species are present. In addition, membrane proteins pose special problems for determination of oligomeric states due to complications arising from the presence of lipid and detergent molecules, and techniques such as cross-linking as reported by Azem et al., 1995, *Biochimica et Biophysica Acta*, 1243:151-156, single molecule subunit counting, as reported by Ulbrich and Isacoff, 2007, *Nat Methods*, 4:319-321, or mass spectroscopy as reported by Barrera et al., 2009, *Nat Methods* 6:585-587, involve difficulties in interpretation or require specialized equipment. Accordingly, there is no gold standard for membrane protein oligomer characterization.

SUMMARY

In some embodiments of the present invention, a method of counting proteins in a protein complex includes tagging a protein of the protein complex to form a tagged protein having a peptide tag and a protease cleavage site between the peptide tag and the protein; expressing the tagged protein in a culture to form a tagged complex having expressed tagged proteins; selectively digesting the expressed tagged proteins with a protease to form an analyte mixture having selectively digested proteins; and analyzing the analyte mixture at at least two different time points to quantify the selectively digested proteins.

In some embodiments, the analyzing of the analyte mixture includes a technique selected from native polyacrylamide gel electrophoresis (PAGE), isoelectric focusing (IEF), or combinations thereof. The PAGE analysis may be clear native PAGE or blue native PAGE. Further analysis of the clear native PAGE or the blue native PAGE may be by Coomassie stain, Western blot, in-gel fluorescence, in-gel luminescence, or combinations thereof. The IEF analysis may be an IEF gel or an IEF strip.

In some embodiments, the protein complex is a membrane protein complex or a soluble protein complex. The protein complex may also include a homo-oligomeric complex or a hetero-oligomeric complex. The protein complex may also be a mixed oligomeric species.

In some embodiments, the peptide tag is a mass tag or a charge tag, or a tag having both mass and charge. In some embodiments, the mass tag has a mass of at least 5 kilodaltons.

In some embodiments, the peptide tag includes fluorescent protein tags, glutathione s-transferase tags, maltose binding protein (MBP), chitin binding protein, cellulose-binding protein, calmodulin binding peptide, streptavidin binding peptide (SBP), poly-arginine, poly-histidine, FLAG (DYKD-DDDK), 3x FLAG, streptavidin (strep)-tag II, c-myc, RNase A S-peptide (S-tag), natural histidine affinity tag (HAT), alkaline phosphatase (ALP), $\beta$-D-galactosidase, $\beta$-D-glucose oxidase, luciferase, peroxidase, and xanthine oxidase.

In some embodiments, the protease cleavage site is cleavable by a protease selected from tobacco etch virus (TEV), human rhinovirus (HRV) 3C, thrombin, Factor Xa, and enterokinase.

In some embodiments, the culture is a cell culture or a cell-free extract. The method of the present invention also includes lysing the cells of the cell culture to form a cell lysate including the expressed tagged protein. In some embodiments, the method also includes isolating the tagged protein from the culture to form an isolated tagged complex.

In some embodiments, the peptide tag has a mass that is different from the mass of the protein.

In some embodiments, the at least two different time points includes a zero time point, an endpoint, and a time point in between the zero time point and the endpoint.

In some embodiments, a method of counting proteins in a protein complex includes tagging a first protein of the protein complex to form a first tagged protein including a first peptide tag and a first protease cleavage site between the first peptide tag and the first protein; tagging a second protein of the protein complex to form a second tagged protein including a second peptide tag and a second protease cleavage site between the second peptide tag and the second protein; expressing both the first tagged protein and the second tagged protein in a culture to form a tagged complex including the first tagged protein and the second tagged protein; selectively digesting the tagged complex with a first protease and a second protease to form an analyte mixture including selectively digested proteins; and analyzing the analyte mixture at at least two different time points to quantify the selectively digested proteins.

In some embodiments, selectively digesting the tagged complex includes selectively digesting the tagged complex with a first protease to form a first analyte mixture of selectively digested proteins; and selectively digesting the tagged complex with a second protease to form a second analyte mixture of selectively digested proteins.

In some embodiments, analyzing the analyte mixture includes analyzing the first analyte mixture prior to selectively digesting the second tagged protein; and analyzing the second analyte mixture after selectively digesting the second tagged protein.

In other embodiments, analyzing the analyte mixture comprises analyzing both the first analyte mixture and the second analyte mixture after selectively digesting the second tagged protein.

In some embodiments of the present invention, a method of counting proteins in a protein complex includes tagging a first protein of the protein complex to form a first tagged protein including a first peptide tag and a first protease cleavage site between the first peptide tag and the first protein; tagging a second protein of the protein complex to from a second tagged protein including a second peptide tag and a second protease cleavage site between the second peptide tag and the second protein; expressing the first tagged protein in a first culture to form a first tagged complex including the first tagged protein; expressing the second tagged protein in a second culture to form a second tagged complex including the second tagged protein; selectively digesting the first tagged complex with a first protease to form a first analyte mixture including first selectively digested proteins; selectively digesting the second tagged complex with a second protease to form a second analyte mixture including second selectively digested proteins; analyzing the first analyte mixture at at least two different time points to quantify the first selectively digested proteins; and analyzing the second analyte mixture at at least two different time points to quantify the second selectively digested proteins.

In some embodiments, a method of counting a plurality of proteins in a protein complex includes tagging the plurality of proteins of the protein complex to form a plurality of tagged proteins, each tagged protein including a peptide tag and a protease cleavage site between each peptide tag and each protein; expressing the plurality of tagged proteins in at least one culture to form a tagged complex including a plurality of expressed tagged proteins; selectively digesting at least one of the plurality of expressed tagged proteins with at least one protease to form at least one analyte mixture including at least one selectively digested protein; and analyzing the at least one analyte mixture at at least two different time points to quantify the at least one selectively digested protein.

In some embodiments of the method of counting a plurality of proteins in a protein complex, the expressing of the plurality of tagged proteins includes expressing the plurality of tagged proteins in a single culture. In other embodiments of this method, the expressing the plurality of tagged proteins comprises expressing each of the plurality of tagged proteins in a separate culture.

In some embodiments of the method of counting a plurality of proteins in a protein complex, selectively digesting the at least one of the plurality of expressed tagged proteins includes selectively digesting all of the plurality of expressed tagged proteins, the at least one protease including a different protease for each of the plurality of expressed tagged proteins.

In some embodiments of the method of counting a plurality of proteins in a protein complex, the at least one analyte mixture includes a separate analyte mixture for each of the at least one selectively digested proteins. In other embodiments of this method, the at least one analyte mixture includes a single analyte mixture including all of the selectively digested proteins.

BRIEF DESCRIPTION OF THE DRAWINGS

FIG. 5 is a protein sequence alignment of purified MtMscL-GFP (SEQ ID NO: 4), SaMscL-GFP (SEQ ID NO: 5), and EcMscL-GFP (SEQ ID NO: 6) proteins, according to embodiments of the present invention.

FIG. 6A is a table listing the masses of a mass tagged MtMscL complex before and after each mass tag is removed according to embodiments of the present invention.

FIG. 6B is a table listing the masses of mass tagged SaMscL complexes before and after each mass tag is removed according to embodiments of the present invention.

FIG. 6C is a table listing the masses of mass tagged EcMscL complexes before and after each mass tag is removed according to embodiments of the present invention.

FIG. 8A is a graph of the probability of reaction cleavage products of a mass subtraction reaction according to embodiments of the present invention.

FIG. 8B is a table listing the probability for each reaction product shown in FIG. 8A according to embodiments of the present invention.

DETAILED DESCRIPTION

Figure 1A:
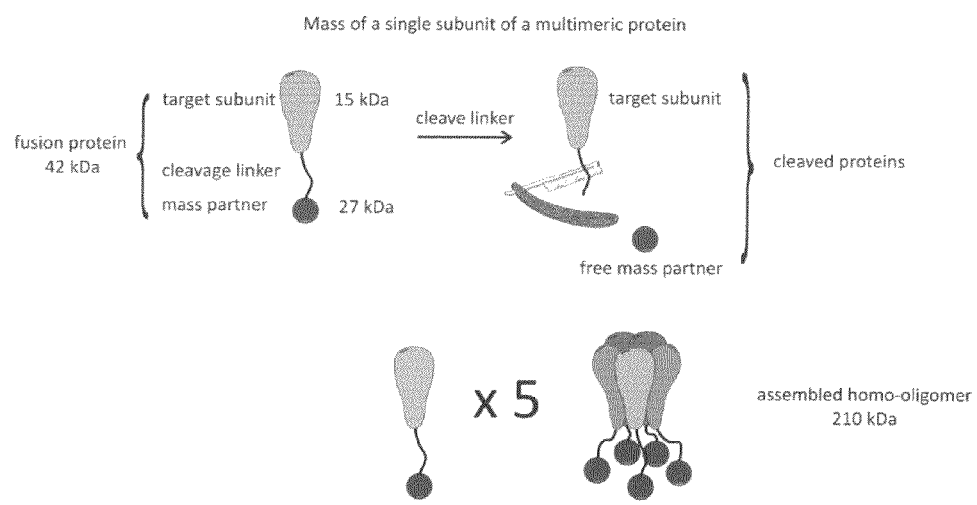
FIG. 1A is a schematic of a mass subtraction method according to embodiments of the present invention.

Aspects of the present invention are directed to methods of counting protein subunits of an oligomeric complex based on the removal of mass and/or charge. Methods according to the present invention are designed to be fast, reproducible with modest amounts of protein, generalizable to membrane and soluble proteins, and experimentally accessible to most protein laboratories. This technique encompasses the removal of both mass and/or charge on protein subunits of homo-oligomeric and hetero-oligomeric complexes.

As used herein, mass/charge refers to mass and charge, as well as mass or charge. As disclosed, some moieties can have both sufficient charge and mass, and therefore, can be analyzed for one characteristic or both.

Also, mass/charge partner and peptide tag are used interchangeably throughout this disclosure including the drawings and claims.

Target protein subunits and protein subunits are also used interchangeably throughout this disclosure including the drawings and claims, and refer to the proteins of an oligomeric complex. The proteins may be of the same protein type (homo-oligomer) or may be of different protein types (hetero-oligomer).

As used herein, mixed oligomeric species refers to a protein complex that includes more than one type of oligomer (e.g., an oligomer that assembles as a pentamer and a tetramer). A mixed oligomeric species may be homo-oligomeric or hetero-oligomeric.

In some embodiments of the present invention, a method of counting the protein subunits of an oligomeric protein complex includes tagging a protein of the protein complex to from a tagged protein having a peptide tag and a protease cleavage site between the peptide tag and the protein. After the protein is tagged with the peptide tag and a protease site, the protein is expressed in a culture to thereby express the protein subunits of the protein complex and form the complex with tagged proteins. The expressed tagged complex is then selectively digested with a protease capable of cleaving at the protease cleavage site to form an analyte mixture having selectively digested tagged proteins. The analyte mixture is analyzed at at least two different time points during the selective digestion to quantify the selectively digested proteins.

Specifically, for hetero-oligomeric complexes, a method of counting proteins in a protein complex, the method includes tagging a first protein of the protein complex to form a first tagged protein having a first peptide tag and a first protease cleavage site between the first peptide tag and the first protein, and tagging a second protein of the protein complex to form a second tagged protein having a second peptide tag and a second protease cleavage site between the second peptide tag and the second protein. The first tagged protein and the second tagged protein are expressed in a culture to form a tagged complex having the first tagged protein and the second tagged protein. The tagged complex is selectively digested with a first protease and a second protease to form an analyte mixture having selectively digested proteins, and the analyte mixture is analyzed at at least two different time points to quantify the selectively digested proteins.

Also, for hetero-oligomeric complexes, a method of counting a plurality of proteins in a protein complex includes tagging the plurality of proteins of the protein complex to form a plurality of tagged proteins, each tagged protein including a peptide tag and a protease cleavage site between each peptide tag and each protein. The plurality of tagged proteins is expressed in at least one culture to form a tagged complex including a plurality of expressed tagged proteins. At least one of the plurality of expressed tagged proteins is selectively digested with at least one protease to form at least one analyte mixture having at least one selectively digested protein, and the at least one analyte mixture is analyzed at at least two different time points to quantify the selectively digested proteins.

Figure 1B:
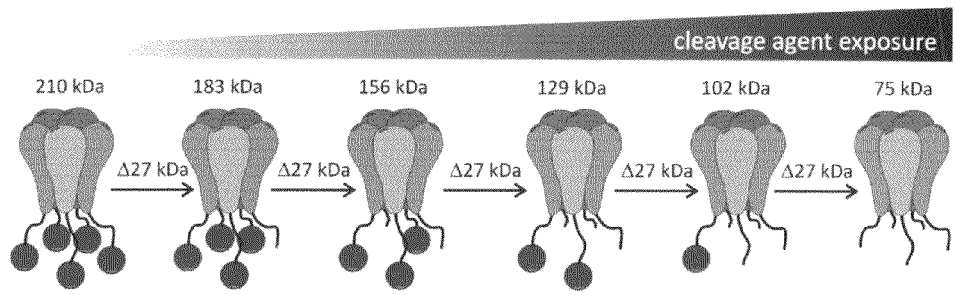
FIG. 1B is a schematic of a mass subtraction method according to embodiments of the present invention.

In FIGS. 1A-1B, a mass subtraction reaction is shown schematically as a protein complex of interest (having target protein subunits) fused with a mass partner (peptide tag). In FIG. 1A, a 15 kDa subunit of a hypothetical pentameric membrane protein is fused to a 27 kDa sGFP (superfolder green fluorescent protein) mass tag via a cleavable protease recognition sequence. The individual fusion subunit has a mass of 42 kDa. The assembled pentameric fusion protein has a mass of 210 kDa. Treatment with the corresponding protease selectively removes an sGFP mass partner from each subunit. FIG. 1B shows the expected reaction products after protease treatment of the pentameric fusion protein. For a pentameric protein, 6 reaction products corresponding to the loss of 0 to 5 mass tags are produced. The reaction products have masses ranging from a fully tagged oligomer of 210 kDa to a fully cleaved oligomer of 75 kDa. By controlling the protease exposure, time points containing all reaction products are produced, and their products may be separated and counted, for example, by PAGE (poly acrylamide gel electrophoresis).

Figure 1C:
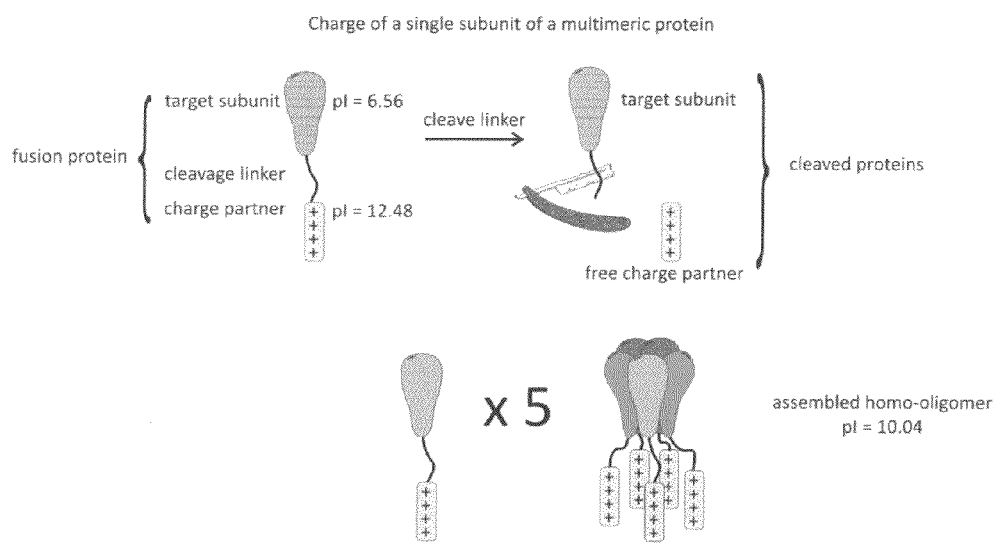
FIG. 1C is a schematic of a charge subtraction method according to embodiments of the present invention.
Figure 1D:
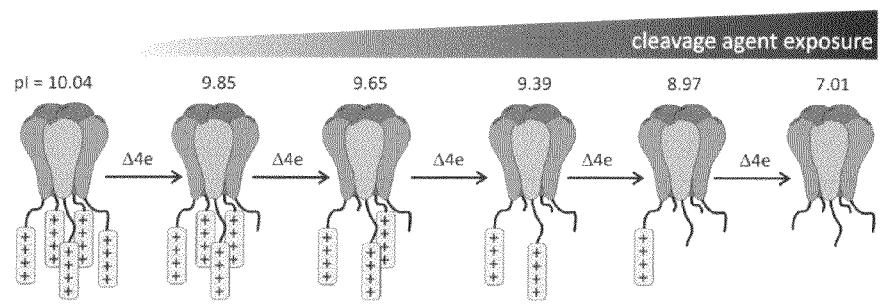
FIG. 1D is a schematic of a charge subtraction method according to embodiments of the present invention.

In FIGS. 1C-1D, a charge subtraction reaction is shown schematically as a protein complex of interest (having target protein subunits) fused with a charged peptide tag. In FIG. 1C, a target subunit having a pI of 6.56 of a hypothetical pentameric membrane protein is fused to a peptide tag having a pI of 12.48 via a cleavable protease recognition sequence. The assembled pentameric fusion protein has a pI of 10.04. Treatment with the corresponding protease selectively removes a charge partner from each subunit. FIG. 1D shows the expected reaction products after protease treatment of the pentameric fusion protein. For a pentameric protein, 6 reaction products corresponding to the loss of 0 to 5 charge tags are produced. The reaction products have charges ranging from a fully tagged oligomer having a pI of 10.04 to a fully cleaved oligomer having a pI of 7.01. By controlling the protease exposure, time points containing all reaction products are produced, and their products may be separated and counted, for example, by isoelectric focusing (IEF).

Tagging with a Mass/Charge Partner

Manipulating the protein sequences of interest to prepare an expression vector having the tagged protein as disclosed herein is well known in the art. Expression vectors for molecular manipulation, cloning, and expression of the protein subunit with a protease site and peptide tag are well known in the art and are available commercially from e.g., Sigma-Aldrich, EMD4Biosciences (Novagen, Merck), Invitrogen, Clontech, and Qiagen.

Mass/Charge Partner (Peptide Tag).

In some embodiments of the present invention, any combination of target protein subunit and mass/charge partner may be used that satisfies the following requirements: 1) the mass/charge partner is sufficiently large to generate resolvable mass or charge shifts upon cleavage, and 2) the mass/charge partner is monomeric so as not to induce or influence oligomerization. For example, for a homo-oligomer of n subunits, the total mass/charge of the fusion protein oligomer is equal to the sum of the masses/charges of n target subunits and n mass/charge partners. In some embodiments, mass/charge is subtracted by partial enzymatic cleavage (i.e., limited proteolysis). Cleavage at a unique protease removes mass/charge partners generating a series of reaction products separated by the mass and/or charge of a single mass/charge partner. A total of n+1 reaction products (corresponding to the loss of 0, 1, 2 . . . n mass/charge partners) are produced.

In some embodiments, any peptide tag that can be expressed as a fusion protein with the protein subunits of the protein complex can be used. In some embodiments, the peptide tag is a mass/charge tag that is a synthetic peptide sequence that is monomeric does not impart impeding activity or influence the assembly of the protein complex. In some embodiments, the peptide mass tag to be cleaved has a mass of at least 5 kilodaltons, such that a fully tagged complex can be resolved from a tagged complex having one tag removed. In some embodiments, the peptide mass tag to be cleaved has a mass of at least 13 kilodaltons. For a subtraction of mass measurement, the selection of a mass tag(s) is determined empirically depending on the type of protein complex. In general, mass tags must be at least 5 kDa and preferably at least 13 kDa to ensure detectable separation by native PAGE. The minimum mass of a mass tag will vary depending on the mass tag itself, as well as the protein complex to be analyzed, and its inherent migration in a native PAGE gel. A person having ordinary skill in the art can empirically determine the minimum mass tag for a particular oligomeric protein complex. For a subtraction of charge measurement, the peptide tag should have sufficient charge (positive or negative) to shift the pI of the target complex so that it can be resolved by isoelectric focusing (IEF).

The peptide tag may be purchased. For example, any fluorescent peptide tag may be used having sufficient mass and/or charge, as disclosed in Smith, 2007, *Nature Methods,* 4:755-761, the entire contents of which are herein incorporated by reference. For example, green fluorescent protein (GFP), red fluorescent protein (RFP), and yellow fluorescent protein (YFP). In addition, chemiluminescent peptide tags may be used and analyzed in gel or in strip or by a colorimetric assay. Examples of chemiluminescent peptide tags and corresponding assays are known in the art, and include alkaline phosphatase (ALP), β-D-galactosidase, β-D-glucose oxidase, luciferase, peroxidase, and xanthine oxidase, as disclosed in Hempen and Karst, 2006, *Anal Bioanal Chem,* 384:572-583, the entire contents of which are herein incorporated by reference. Other commercially available peptide tags include glutathione s-transferase (GST), maltose binding protein (MBP), chitin-binding protein, cellulose-binding domains, poly-arginine, poly-histidine, FLAG (DYKDDDDK), 3x FLAG, strep-tag II, c-myc, S-tag (RNase A S-peptide), HAT (natural histidine affinity tag), calmodulin binding peptide, and SBP (streptavidin binding protein), as described in Terpe, 2003, *Appl Microbiol Biotechnol.,* 60:
523-533, the entire contents of which are herein incorporated by reference.

Protease and Protease Recognition Sequence

The mass/charge partner may be added via a short linker containing a unique protease recognition site so that it is expressed as a fusion with the target protein. For removal of the peptide tag, a protease site is positioned between the protein subunit and the peptide tag. The initial mass/charge of the oligomer is then composed of the mass and/or charge of the untagged oligomer plus the added masses/charges of the mass/charge partners (FIGS. 1A-1D).

In some embodiments, the protease site is any unique protease site that upon cleavage with a protease will result in the cleavage of the fusion protein between the peptide tag and the target protein subunit. Any protease and corresponding protease cleavage site may be used, (for example, any viral protease, e.g. the tobacco etch virus (TEV) protease or the human rhinovirus (HRV) 3C protease, as described herein and Cordingley et al., 1990, *JBC,* 265: 9062-9065; Rawlings et al., 2009, *Nucleic Acids Res.,* 38:D227-D233, the entire contents of each of these references are herein incorporated by reference. Other proteases include thrombin, Factor Xa, and enterokinase, as described in Degen et al.1987, *Biochemistry,* 26:6165-6177; Messier et al., 1991, *Gene,* 99:291-294; and Huang et al., 2007, *Prep. Biochem. Biotechnol.,* 37:205-217, the entire contents of all of these references are herein incorporated by reference.

Partial protease cleavage of the peptide tag results in the release of each peptide tag from each protein subunit in a time-dependent manner. Accordingly, the number of peptide tags released corresponds to the number of protein subunits in the oligomeric complex. In some embodiments, the distribution of reaction products as a function of the protease activity is observed by comparing at least two time points throughout the proteolysis reaction. In some embodiments, at least three time points are compared. These time points may include the endpoint at which the protease digestion is complete. In some embodiments, one time point includes a time between a zero time point and the endpoint. The zero time point is the time prior to the addition of a protease to the tagged fusion protein. Complete digestion is determined empirically for each protease and each mass/charge partner, and is easily determined by a person having ordinary skill in the art. An example of complete digestion is disclosed in the Examples and shown, for example, in FIGS. 7B, 9B, 10B, and 13A.

Expression of the Tagged Protein Complex

In some embodiments, the tagged protein complex is expressed in any culture suitable for expression of the selected expression vector(s). Suitable cell expression systems include bacteria, yeast, insect cells, and mammalian cell systems, as described in *The QIAexpressionist*, June 2003, the entire contents of which are herein incorporated by reference. Cell-free extracts may also be used for expression of the tagged proteins, as described in Schwarz et al. 2007, *Methods*, 41:355-369, the entire contents of which are herein incorporated by reference.

In some embodiments, after expression of the tagged complex, a cell lysate is prepared, and the partial protease digest is performed on the cell lysate. Accordingly, in order to elucidate the reaction products, the digested cell lysate is separated by native PAGE and analyzed by Western blot using antibodies to the protein subunit(s) and/or the peptide tag, or blotted to detect fluorescence or chemiluminescence depending on the type of peptide tag selected.

In some embodiments, the tagged protein complex is isolated from the cell lysate or cell-free extract using any suitable purification method. For example, as disclosed herein (e.g., Examples, FIG. 5), MscL-sGFP proteins may be expressed with an N-terminal poly-histidine tag for purification.

Figures 3A, 3B:
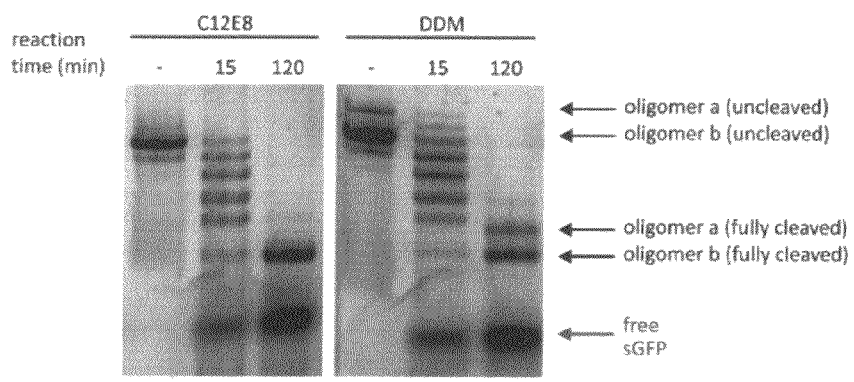
FIG. 3A is a blue native polyacrylamide gel electrophoresis (BN-PAGE) showing exemplary analysis results of mass subtraction according to embodiments of the present invention.
FIG. 3B is a table showing compatibility of detergents for mass subtraction using SaMscL(CΔ26)MscL according to embodiments of the present invention.

In addition, detergents used for purification must be compatible with protein stability, PAGE migration, and protease activity as disclosed in Mohanty et al., 2003, *Expr Purif* 27: 109-114, the entire contents of which are herein incorporated by reference (FIGS. 3A-3B). These concerns are protein specific and must be empirically determined. In the case of SaMscL(CΔ26), the protein was measured by the present subtraction method in several detergents (FIG. 3B) as a mixture of tetramers and pentamers. However, for EcMscL, the choice of detergent affected the measured oligomeric state indicating that detergent extraction or detergent interaction with Coomassie favors one oligomeric form (FIG. 3A). It has been shown that Coomassie interaction with protein in a BN PAGE does not perturb the oligomeric state as described in Schagger et al., 1994, *Anal Biochem* 217:220-230).

Analysis of Selectively Digested Proteins

In some embodiments, the separation of mass tags includes native PAGE analysis. In some embodiments, the PAGE is blue native (BN) PAGE or clear native (CN) PAGE. For membrane protein complexes, BN PAGE may be more effective for separation. For soluble protein complexes, CN PAGE or BN PAGE may be used. Protein staining of CN PAGE includes any suitable protein stain, including Coomassie, silver stain, etc. Alternatively, when the peptide tag(s) is fluorescent or chemiluminescent, the fluorescence and/or luminescence will be detected on the CN-PAGE without additional staining by in gel/in blot fluorescence/luminescence.

In some embodiments, the separation of charge tags includes clear native PAGE for soluble protein complexes. For membrane or soluble proteins, the charge tags may be separated by isoelectric focusing (IEF), as described in Zilberstein et al., 2010, *Electrophoresis*, 31:1747-1753; Friedman et al., 2009, *Methods Enzymol*, 463:515-540; Gianazza et al., 2009, *Electrophoresis*, Suppl. 1:S112-S1121; and Sommer et al., 2009, *Electrophoresis*, 30:742-757, the entire contents of each of these references are herein incorporated by reference. In some embodiments, IEF includes an IEF gel or IEF strip. The IEF gel or IEF strip may be further analyzed by Coomassie stain, Western blot or in gel/in blot/in strip fluorescence/luminescence. In some embodiments the charge tags are analyzed using ion exchange chromatography.

Analyzing both Charge and Mass

As would be understood by a person having ordinary skill in the art, some peptide tags can be used as either a mass partner or a charge partner, and could also be used for the loss of both mass and charge. For example, the GFP tag can be expressed as a fusion protein with a target protein subunit having a cleavage site between the GFP tag and the target protein. After expression of the target protein with the GFP tag, limited proteolysis is performed and samples of the proteolyzed mixture are taken at time points, and can be separated on native PAGE to resolve and analyze the reaction products by mass. Alternatively, or additionally, the digested GFP-tagged samples could also be resolved by IEF, for example by IEF gel, IEF strip, or ion exchange chromatography.

Hetero-Oligomeric Protein Complexes

Figure 2A:
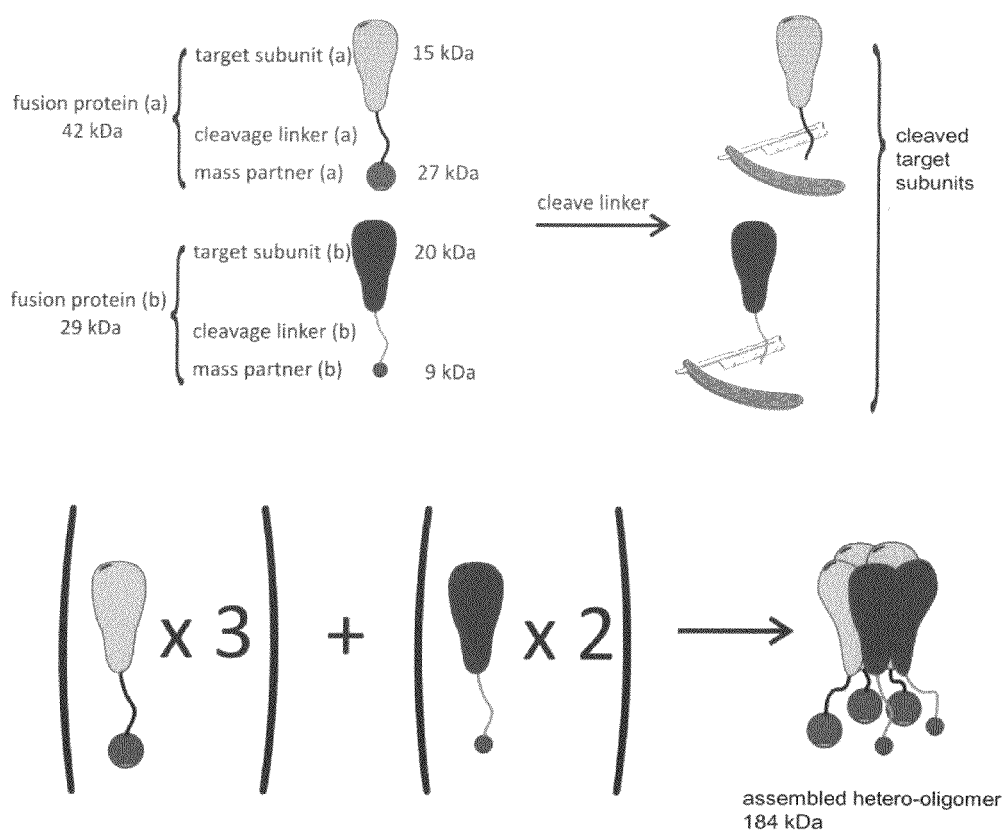
FIG. 2A is a schematic of a mass/charge subtraction method for a hetero-oligomeric complex according to methods of the present invention.
Figure 2B:
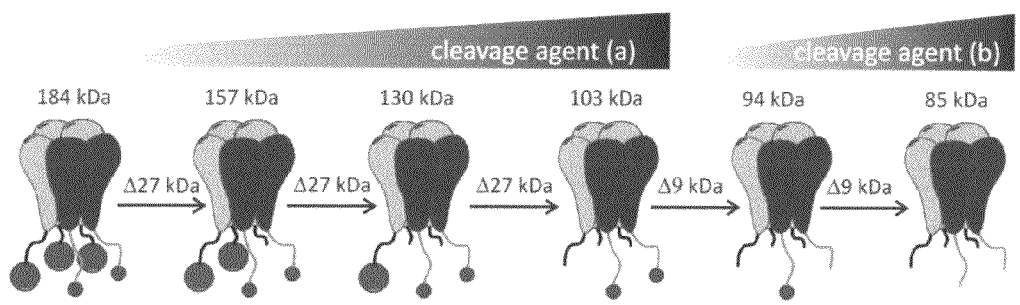
FIG. 2B is a schematic of a mass/charge subtraction method for a hetero-oligomeric complex according to methods of the present invention.

In some embodiments, the subtraction of mass/charge includes tagging and limited proteolysis of a hetero-oligomeric complex having more than one type of protein subunit. A hetero-oligomeric complex made of two different proteins is shown in FIGS. 2A-2B. This method also applies to a hetero-oligomeric complex having more than two different proteins. That is, expression of each protein type as a fusion protein of a peptide tag having a unique cleavage site resolves the separate subunits upon partial cleavage, as disclosed herein. Additionally, the peptide tags can be the same or different for each type of protein subunit so long as the cleavage sites for each type of protein subunit are unique.

In some embodiments, the tagged hetero-oligomeric complex is expressed with only one protein type tagged in each culture. For example, for a protein complex of protein A and protein B, a tagged protein A may be expressed in one culture and a tagged protein B may be expressed in a second culture. The partial digestion steps and analysis may then be carried out on each cell lysate or each isolated complex. In other embodiments, the tagged hetero-oligomeric complex is expressed with all proteins of the complex tagged in one culture. If the peptide tag is the same for both proteins, separate expression and culturing of the tagged proteins would be necessary for effective analysis.

As would be understood by a person having ordinary skill in the art, the complexes having more than one type of protein may be selectively digested sequentially one protease at a time, or separately, depending on whether or not all tagged proteins are expressed in the same culture. Additionally, the partial digestion of more than one protease may be simultaneous, as long as the conditions required for the proteases are compatible. The digested mixtures may be analyzed after partial digestion with one protease, followed by subsequent digestion with a second (or third or fourth) protease, where the second (or third or fourth) digestion is followed by analysis. Moreover, the digested mixtures that are digested sequentially to faun one digested analyte mixture or separately to form separate analyte mixtures may be analyzed separately or together. The sequence of steps for digestion and analysis may be ordered as determined most effective for the number of tagged proteins and selected expression strategy in a culture or cultures.

The following Examples are presented for illustrative purposes only, and do not limit the scope or content of the present application.

EXAMPLES

Determining the Oligomeric State of MscL, Channel Complex

The following examples are disclosed in Gandhi et al., 2011, *Protein Sci*, 20:313-326, the entire contents of which are herein incorporated by reference.

The mechanosensitive channel of large conductance (MscL) is a homo-oligomeric, stretch-activated membrane protein responsible for regulating osmotic pressure in bacteria and archaea. The MscL channel acts as an emergency release valve that activates when cells are placed under osmotic stress. Increasing membrane tension stabilizes the channel's open form leading to the formation of a non-selective pore with an open channel conductance orders of magnitude greater than ion-selective channels. When the gene product for the *E coli* MscL (EcMscL) was identified as a protein of 136 amino acids, it was recognized that MscL must form a homo-oligomer to create such a high conductance channel as reported by Sukharev et al., 1994, *Nature*, 368: 265-268. Early cross-linking and electron microscopy studies indicated that EcMscL formed hexamers, but this view was subsequently revised when the crystal structure of the *Mycobacterium tuberculosis* (MtMscL) channel revealed a pentamer as reported by Chang et al., 1998, Science 282:2220-2226; Steinbacher et al., Structures of the prokaryotic mechanosensitive channels MscL and MscS. In: Hamill OP, Ed. (2007) *Current Topics in Membranes Mechanosensitive Ion Channels, Part A*. Academic Press, London, pp. 1-24.

The view that all MscL channels are pentamers was recently challenged by the crystal structure of a C-terminal truncation of *Staphylococcus aureus* MscL (SaMscL(CΔ26)) which revealed a tetramer (FIG. 4A), as reported by Liu et al., 2009, *Nature* 461:120-124. Reflecting their high sequence similarity (FIG. 4B), EcMscL, MtMscL, and SaMscL(CΔ26) all form functional tension gated channels with similar open channel conductances as reported by Moe et al., 1998, *Mol Microbiol* 28:583-592; Liu et al., 2009, *Nature* 461:120-124. Additionally, all three homologs and wild-type SaMscL are able to rescue cells in osmotic down shock assays, as reported by Moe et al., 2000, *J Biol Chem* 275:31121-31127; Liu et al., 2009, *Nature* 461:120-124.

Figure 4A:
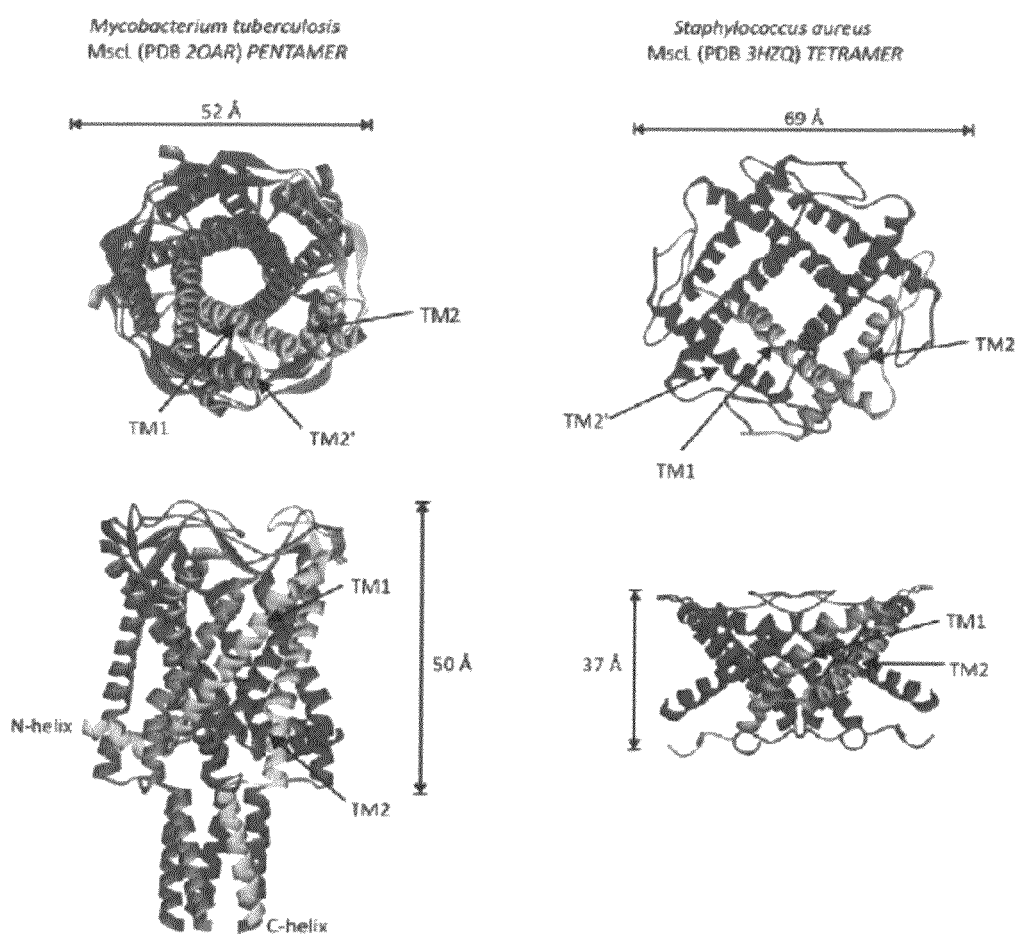
FIG. 4A is a set of crystal structure schematics of pentameric *Mycobacterium tuberculosis* mechanosensitive channel (MtMscL) and tetrameric *Staphylococcus aureus* MscL (SaMscL).
Figure 4B:
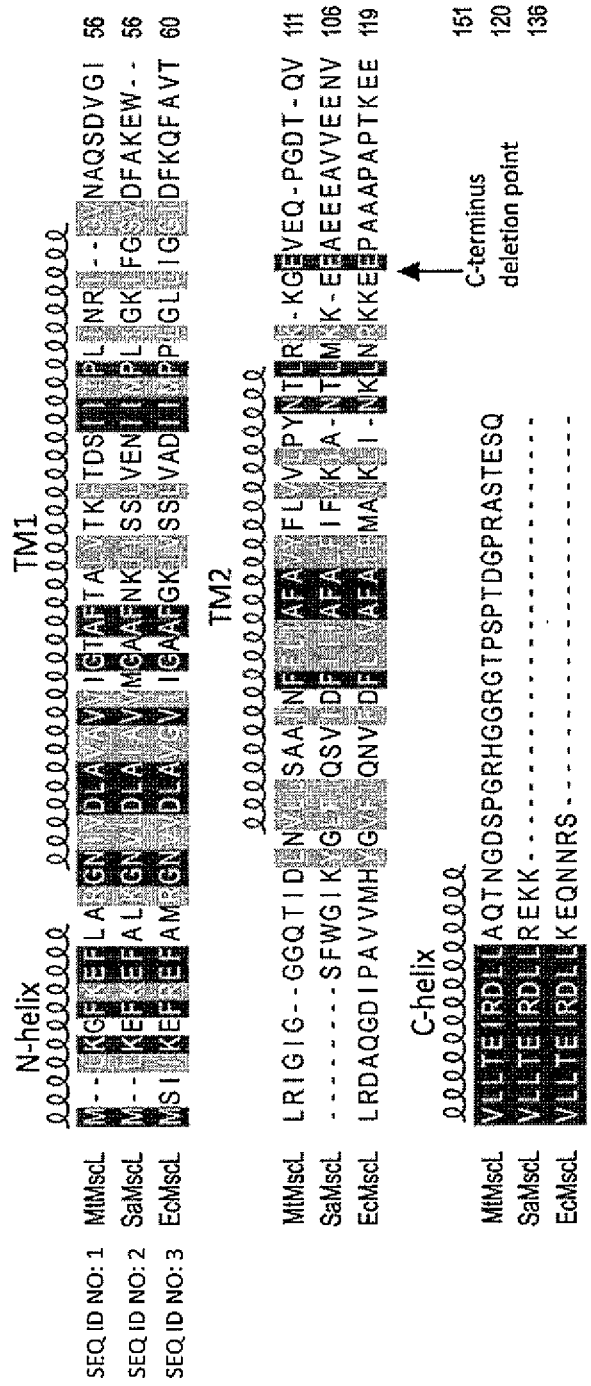
FIG. 4B is a sequence alignment of MtMscL (SEQ ID NO: 1), SaMscL(SEQ ID NO: 2), and *E. coli* MscL (EcMscL) (SEQ ID NO: 3) proteins.

As shown in FIGS. 4A and 4B, related MscL channels demonstrate oligomeric diversity despite high sequence identity. FIG. 4A shows the crystal structures of pentameric MtMscL (PDB: 2OAR) and tetrameric SaMscL(CΔ26) (PDB: 3HZQ). The structures have different dimensions and oligomeric states. The MtMscL pore is less expanded than SaMscl when viewed from the extracellular side of the membrane (top panels) and shorter when viewed from the side (bottom panels). Each MscL subunit is composed of two membrane spanning helices (TM1 and TM2). TM1 lines the channel pore and packs against the TM2 from an adjacent subunit (TM2').

FIG. 4B shows an alignment of the MscL proteins used in this disclosure. Dark and light blue residues correspond to identity and similarity, respectively. The N-helix, TM1, TM2, and C-helix of Mt, Sa, and EcMscL are 46, 32, 22, and 71% identical, respectively. The TM helices have a combined identity and similarity of 63%. Deletion constructs were truncated at the conserved C-terminus glutamate residue.

Given their high sequence relatedness and functional similarity, the structural results raise intriguing questions as to the assembly and activation of MscL channels. The following characterizes the oligomeric state of different MscL constructs to address whether the crystal structures accurately reflected the oligomeric state of these proteins in solution.

In the following examples, mass subtraction is used to count protein subunits by the removal of mass from a protein oligomer through selective partial proteolysis. The proteolysis was quenched at several time points, and the cleavage products were separated via blue native polyacrylamide gel electrophoresis (BN-PAGE). By using the detergent mimic Coomassie blue dye to maintain membrane protein solubility and confer an overall negative charge, BN-PAGE has the important property of separating native membrane protein complexes on the basis of size as disclosed in Stenberg et al., 2005, *J Biol Chem* 280:34409-34419; Wittig et al., 2006, *Nature protocols* 1:418-428; Ma et al., 2008, *Journal of applied crystallography* 41:1150-1160, all of which are incorporated by reference in their entirety. The number of reaction products observed is dependent on the oligomeric state of the protein.

MtMscL is a Pentamer using Mass Subtraction

A mass partner was fused to the C-terminus of MtMscL by fusing a monomeric, superfolder variant of GFP (sGFP) via a short linker containing a TEV protease recognition site (. . . SASGENFLYQ . . .) (FIG. 5). The protein sequences of purified MtMscL-GFP, (SEQ ID NO: 4), SaMscL-GFP (SEQ ID NO: 5), and EcMscL-GFP (SEQ ID NO: 6) including the N-terminal poly-histidine purification tag, TEV protease cleavage site, and the C-terminal sGFP mass tag are shown in FIG. 5. The underlined sequence corresponds to MscL. The position of the SaMscL(CΔ26) and MtMscL(CΔ49) truncations are noted by a red arrow. The sGFP tag (SLSKG . . . DELYK) is approximately 26.8 kDa.

The sGFP variant contains an A206V mutation which removes GFP's tendency to form weak dimers at high concentrations by disrupting the dimerization interface as described in Pedelacq et al., 2006, *Nat Biotechnol* 24:79-88, the entire content of which is herein incorporated by reference. The sGFP mass partner adds approximately 27 kDa to each MscL subunit (FIG. 1A). Over-expression, membrane solubilization in the detergent n-dodecyl-β-D-maltoside (DDM), and purification by metal affinity chromatography yielded a single band on an SDS gel and a single size exclusion chromatography peak (not shown). The purified fusion protein was partially proteolyzed with TEV protease removing some but not all of the sGFPs fused to MtMscL. A complete proteolysis was also performed to ensure total removal of sGFP. The reactions were quenched and their products separated via BN-PAGE in order to preserve non-covalent interactions in the oligomer and separate the reaction products by size. The gel was then stained and examined visually or analyzed in detail by densitometry measurements.

Figure 7A:
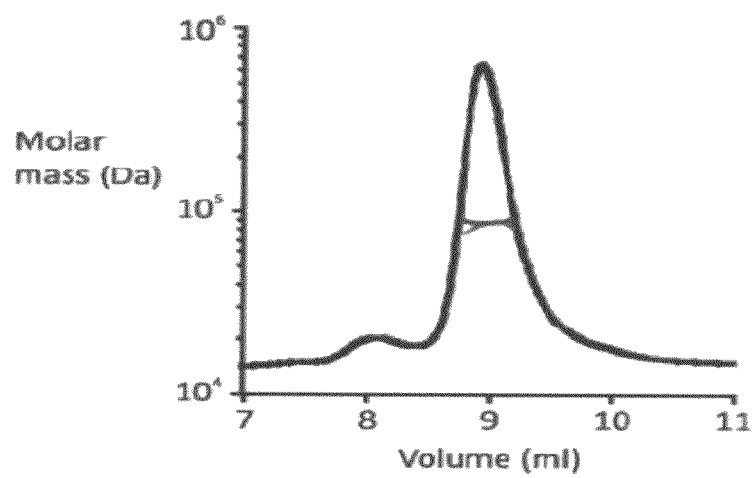
FIG. 7A is an elution profile of MtMscL from size-exclusion chromatography and multi-angled light scattering (SEC-MALS).
Figure 7B:
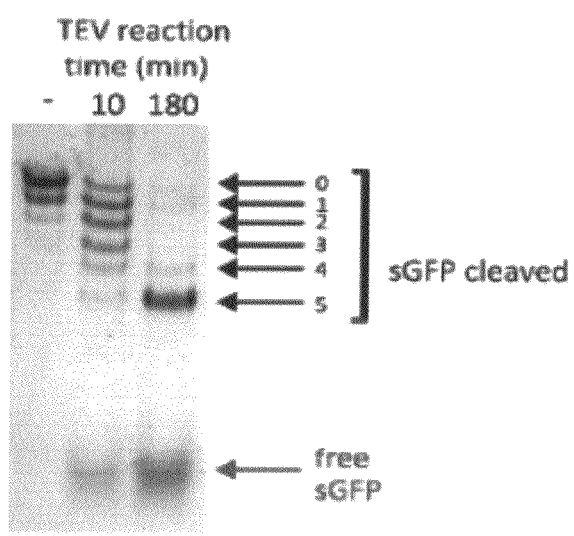
FIG. 7B is a BN-PAGE of mass tagged MtMscL after mass subtraction according to embodiments of the present invention.
Figure 7C:
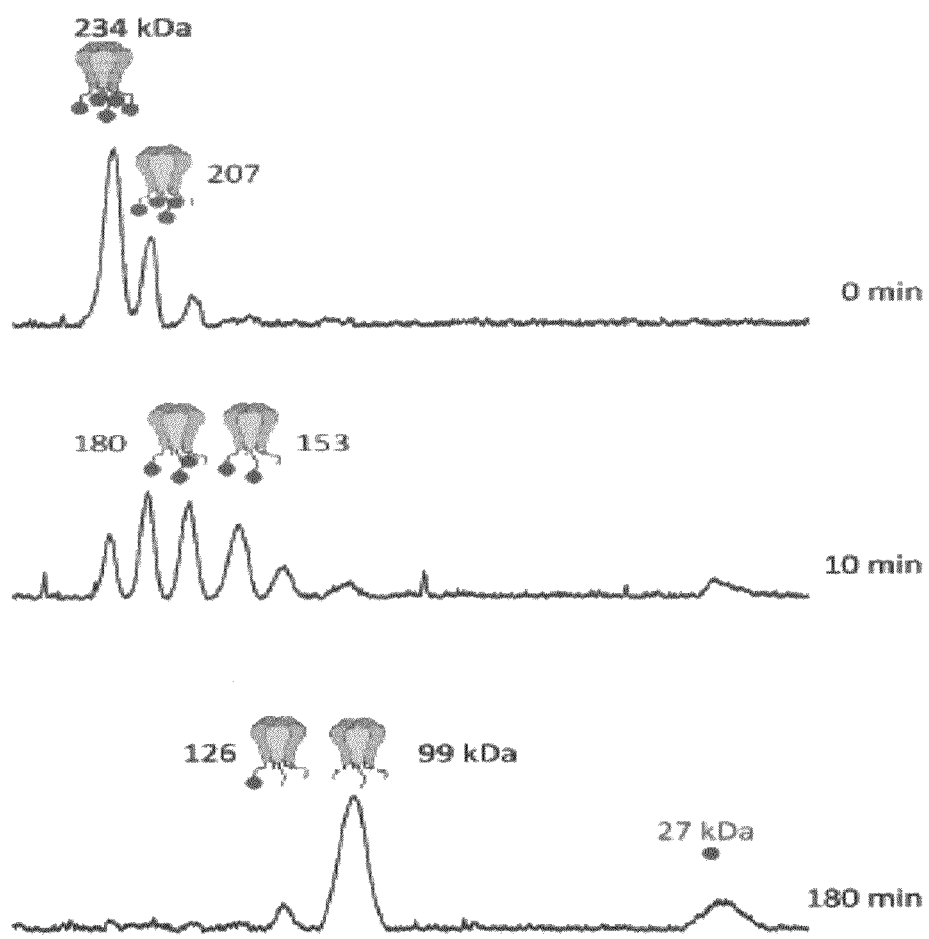
FIG. 7C is a comparison of densitometry traces of the BN-PAGE of FIG. 7B at 0, 10, and 180 minutes, with schematics of the corresponding tagged/untagged complex according to embodiments of the present invention.

FIGS. 7B and 7C show the evolution of reaction products as a function of time. FIG. 7B shows BN-PAGE separation of the reaction products. MtMscL sGFP fusion starting material was run alongside TEV protease reactions quenched at 10 and 180 min. A family of six reaction products corresponding to the loss of 0 to 5 sGFP mass tags are observed. The cleaved sGFP is observed at a lower gel migration distance. At the initial time point, >60% of the protein runs as a single band corresponding to the mass of the entire fusion protein complex. Below the major band are two smaller bands representing the loss of 1-2 sGFP mass tags. The relative proportion of these bands may be interpreted in terms of a binomial distribution consistent with <10% loss of sGFP, presumably due to proteolytic activity in the host cell (FIGS. 8A-8B). FIG. 8B shows the percentage of subtraction of mass reaction products at different cleavage probabilities. Increasing TEV protease exposure results in a ladder of 6 bands consistent with the pentameric structure observed in the crystal structure (FIG. 7B). The bands correspond to the full mass complex (top band, 0 sGFPs lost), the serial loss of 27 kDa due to the proteolytic cleavage of increasing numbers of sGFP (middle bands, 1-4 sGFPs lost), and the completely cleaved MtMscL target protein (bottom band, 5 sGFPs lost). A low molecular weight band corresponding to free sGFP is also seen in the later and final time points. Gel densitometry of the reaction time course reveals that all reaction bands are well separated and identifiable. Nearly all cleavage products are observed by 10 minutes, and cleavage is complete before 3 hours (FIGS. 7B and 7C). FIG. 7C shows densitometry traces of the BN-PAGE bands in FIG. 7B. Cartoons marking each peak show the expected reaction product and its theoretical mass.

As an independent check on the oligomeric state, SEC-MALS measurements were performed on the non-fusion form of MtMscL. The measured mass is in good agreement with mass subtraction measurements (FIG. 7A and Table 1). FIG. 7A shows the elution profile of purified MtMscL examined by SEC-MALS. The red and blue lines correspond to SEC-MALS calculated protein mass and modifier (lipid and detergent) mass respectively.

TABLE 1

Oligomeric states of MscL proteins by different methods

|  | X-ray crystallography | OCAM | sub-units | SEC-MALS protein mass (kDa) ± stdev | SEC-MALS modifier mass (kDa) ± stdev |
|---|---|---|---|---|---|
| MtMscL | 5 | 5 | 4.7 | 87.4 ± 1.0 | 89.4 ± 2.0 |
| MtMscL(CΔ49) |  | 5 |  |  |  |
| SaMscL |  | 5 | 4.6 | 72.9 ± 0.5 | 92.1 ± 0.8 |
| SaMscL(CΔ26) | 4 | 5/4 mixture | 3.6 | 46.5 ± 1.6 | 80.4 ± 1.9 |
| EcMscL |  | 6/5 mixture | 6.0 | 103.0 ± 3.1 | 91.5 ± 7.1 |

SaMscL is a Pentamer by Mass Subtraction

Figure 9A:
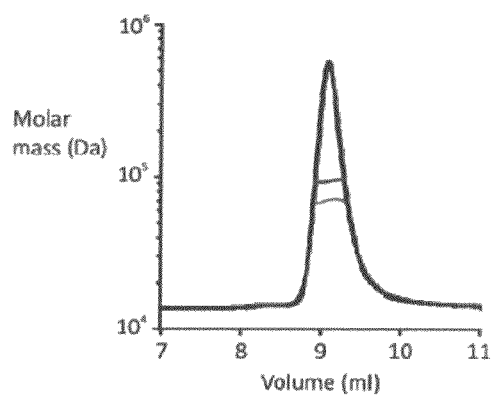
FIG. 9A is an elution profile of SaMscL from size-exclusion chromatography and multi-angled light scattering (SEC-MALS).
Figure 9B:
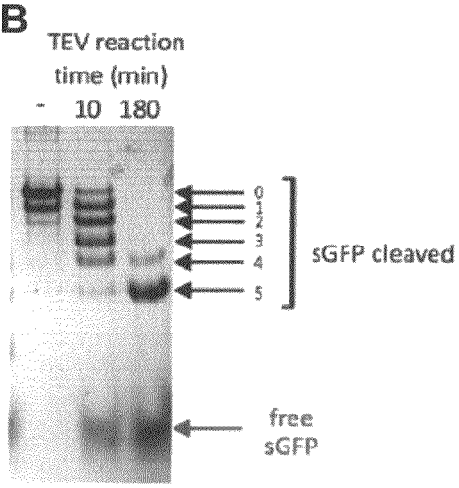
FIG. 9B is a BN-PAGE of mass tagged SaMscL after mass subtraction according to embodiments of the present invention.
Figure 9C:
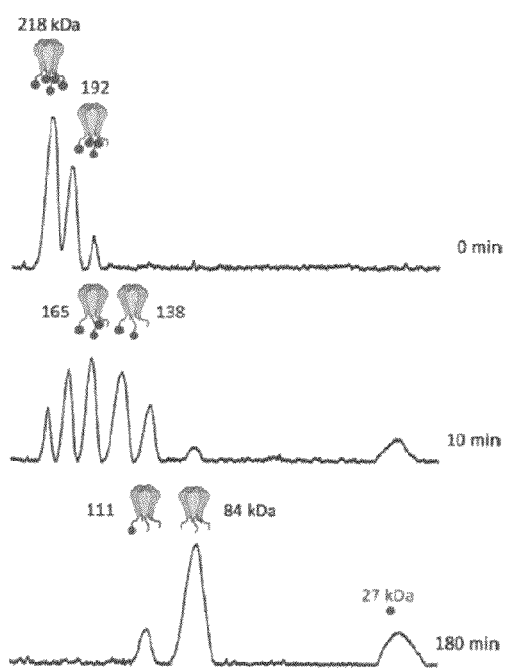
FIG. 9C is a comparison of densitometry traces of the BN-PAGE of FIG. 9B at 0, 10, and 180 minutes with schematics of the corresponding tagged/untagged complex according to embodiments of the present invention.

Having tested the mass subtraction procedure on MtMscL, the SaMscL homolog was then analyzed. SaMscL shares 34% identity to MtMscL (FIG. 4B). Like its Mt counterpart, SaMscL forms a tension activated non-selective channel. The structure of wild-type SaMscL has not been determined by crystallography; however, a C-terminal deletion (SaMscL (CΔ26)) has been solved in a tetrameric form, and previous cross-linking experiments suggested that wild-type SaMscL may also be tetrameric, as described in Liu et al., 2009, *Nature* 461:120-124, the entire content of which is herein incorporated by reference. Mass subtraction was used to determine the oligomeric state of wild-type SaMscL in solution. As with MtMscL, SaMscL was fused to sGFP via a linker containing a TEV protease recognition site. The fusion protein was over-expressed and extracted in DDM. Purification by metal affinity chromatography yielded a single band on an SDS gel and a single size exclusion chromatography peak (not shown). The purified protein was subject to partial and complete proteolysis by TEV protease. FIGS. 9B and 9C shows the mass subtraction reaction products separated by BN-PAGE and identified by densitometry. A ladder of six reaction products and free sGFP was observed, consistent with a pentameric assembly (FIG. 6B, FIG. 9B). SEC-MALS measurement of the non-fusion protein is in good agreement with the pentameric assignment by the subtraction method as disclosed herein (FIG. 9A and Table 1). In FIG. 9A, the red and blue lines correspond to SEC-MALS calculated protein mass and modifier (lipid and detergent) mass respectively. FIG. 9B shows a BN-PAGE separation of the reaction products of the SaMscL. The SaMscL sGFP fusion starting material was run alongside TEV protease reactions quenched at 10 and 180 min. A family of six reaction products corresponding to the loss of 0 to 5 sGFP mass tags is observed. The cleaved sGFP is observed at a lower gel migration distance. FIG. 9C shows the densitometry traces of FIG. 9B. Cartoons marking each peak show the expected mass subtraction reaction product and its theoretical mass.

A C-terminal Deletion of SaMscL Exists as a Mixture of Oligomeric Species

Figure 10A:
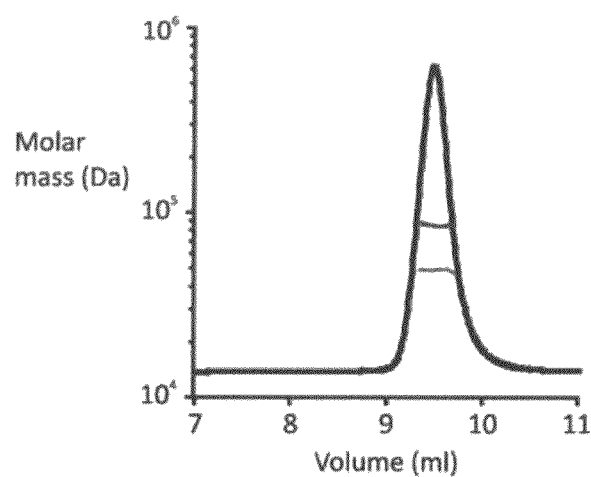
FIG. 10A is an elution profile of SaMscL(CΔ26) from size-exclusion chromatography and multi-angled light scattering (SEC-MALS).
Figure 10B:
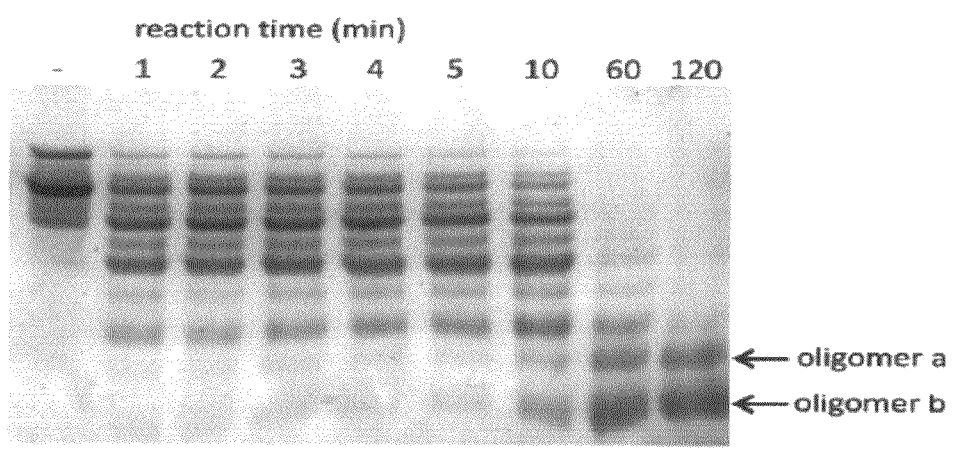
FIG. 10B is a BN-PAGE separation of mass tagged SaMscL(CΔ26) after mass subtraction according to embodiments of the present invention.
Figure 10C:
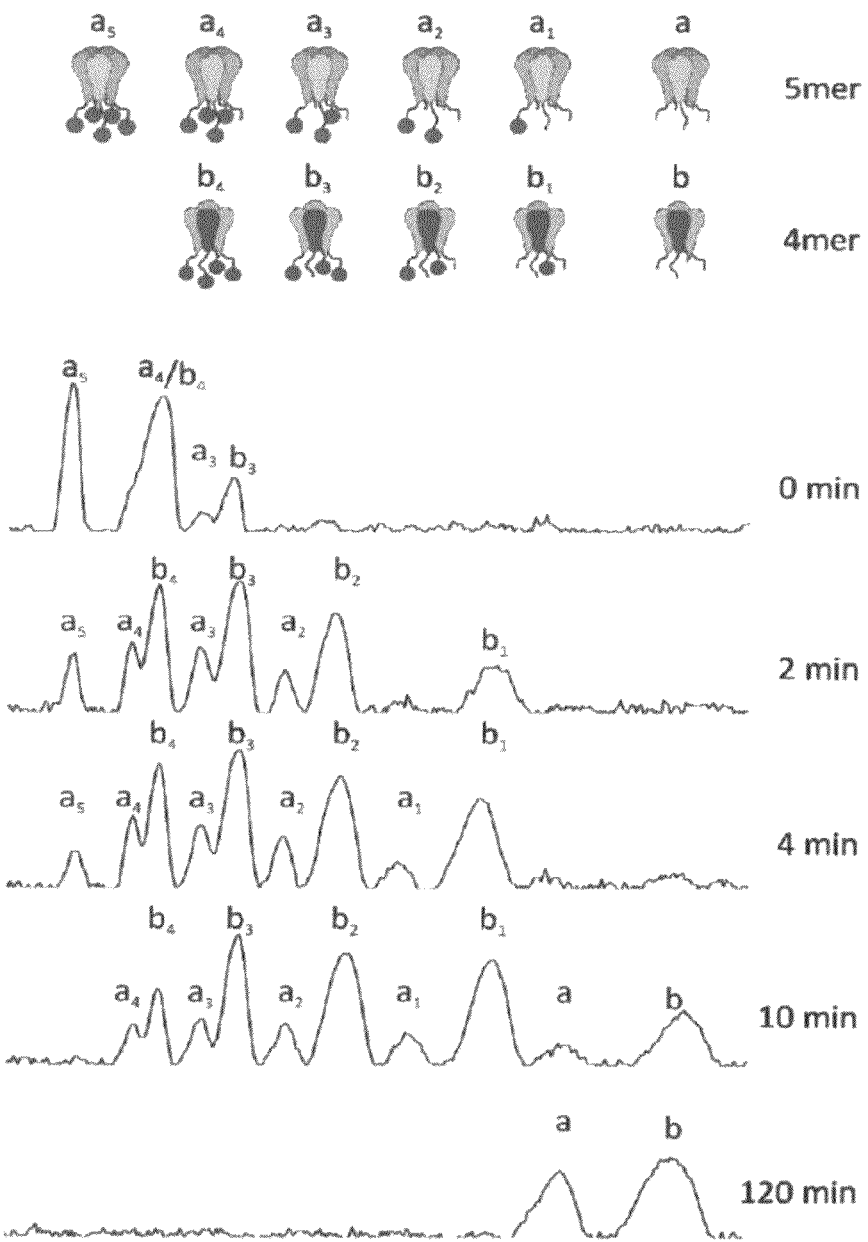
FIG. 10C is a comparison of densitometry traces of the BN-PAGE of FIG. 10B at 0, 2, 4, 10, and 120 minutes, with schematics of the corresponding tagged/untagged complex according to embodiments of the present invention.
Figure 11A:
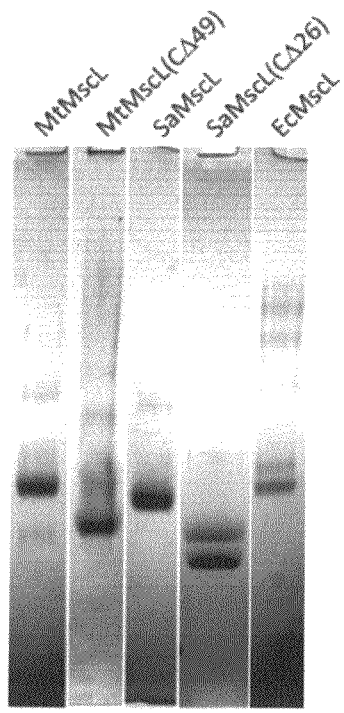
FIG. 11A is a BN-PAGE of MtMscL, MtMscL (CΔ49), SaMscL, SaMscL (CΔ26), and EcMscL according to embodiments of the present invention.

To investigate the oligomeric state of a C-terminal truncation mutant of SaMscL (SaMscL(CΔ26)) in solution, the fusion protein was over-expressed, purified in DDM, and subject to partial and complete proteolysis by TEV protease. The untreated sample runs as a single band on an SDS gel and as a single peak by size exclusion chromatography; however, when the purified protein was analyzed with BN-PAGE two distinct major bands are present (FIG. 10B). This behavior is also observed for the non-fusion SaMscL(CΔ26) (FIG. 11A). When the sGFP fusion is subject to a partial TEV protease digestion and separated by BN-PAGE, the n+1 ladder bands expected for a single tetrameric or pentameric species were not observed despite numerous purification attempts. In contrast to wild type Mt and SaMscL, complex mixture of >6 reaction products (FIG. 10C) was observed. Several intermediate peaks in the gel densitometry are present and offset from major peaks by small gel shifts (FIG. 10C). The final reaction product results in two distinct bands of different apparent masses. Densitometry identifies 11 distinct bands across all time points, excluding free sGFP (FIG. 10C).

Figure 10D:
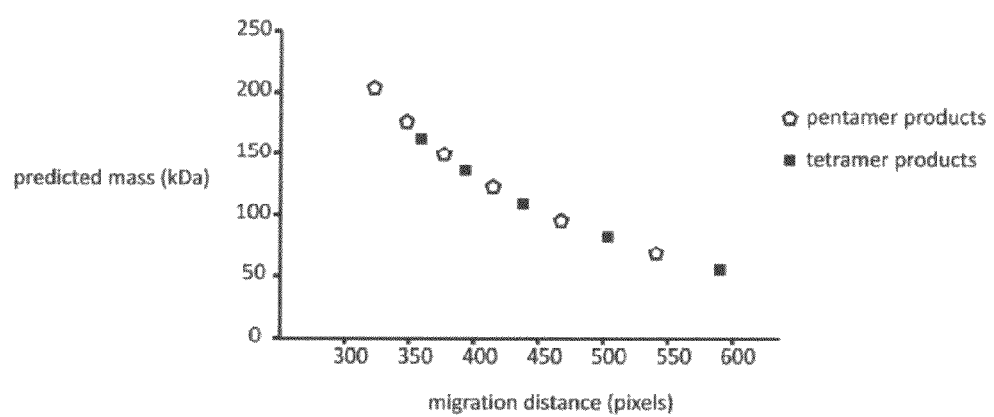
FIG. 10D is a graph of the migration distances of the mass subtraction reaction products from FIG. 10B plotted against the masses of the pentamer and tetramer complexes according to embodiments of the present invention.

Given that the wild-type SaMscL was purified as a pentamer and the C-terminal deletion was crystallized as a tetramer, the observed mass subtraction band pattern was analyzed to determine if the pattern was consistent with a mixture of pentamers and tetramers. A mixed population of pentameric and tetrameric channels should produce exactly 11 products (6 products for the pentamer, 5 products for the tetramer). Assuming the BN-PAGE conditions separate the reaction products predominately by size, it was predicted that two ladders of digestion products with the ladder of pentamer products are offset from the tetramer ladder by the mass of a single MscL subunit. Indeed, measuring the peak position for each reaction product revealed that the product ladders are offset by an average of 26 pixels which is consistent with the 13.8 kDA mass of a single SaMscL(CΔ26) subunit. Additionally, the predicted tetramer peaks migrate ~50% of the distance between the predicted pentamer peaks consistent with 13 kDa and 13.8 kDa difference between these products FIG. 10D. Finally, when the peak positions of the pentamer ladder are plotted against their predicted masses, the masses of the tetrameric ladder lie on the same curve (FIG. 10D). These results suggest that the truncation mutant, at least under the reported expression and purification conditions, exists as both tetramers and pentamers in solution.

The sGFP Mass Tag does not Alter the Oligomeric States of SaMscL(CΔ26)

Figure 12:
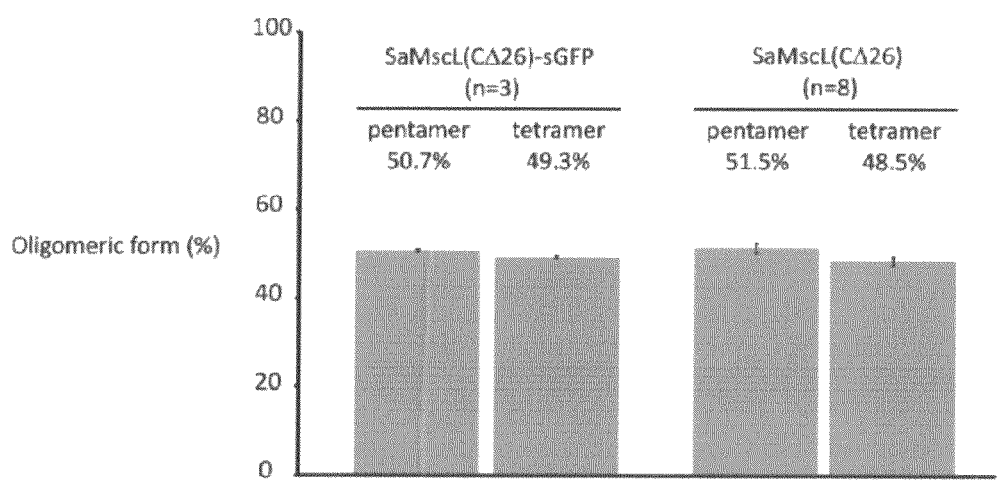
FIG. 12 is a graph of the observed oligomeric forms of untagged SaMscL (CAΔ26) and tagged SaMscL(CΔ26)-sGFP according to embodiments of the present invention.

The next step was to investigate if the observed SaMscL (CΔ26) oligomeric mixture may have been caused by the presence of the sGFP mass tag. Free sGFP is monomeric, and should not induce oligomerization on its own. However, it is possible that the MscL-sGFP fusion may alter the assembly of the fusion protein complex. To test this possibility, we ran BN-PAGE gels of purified SaMscL(CΔ26) lacking a sGFP mass tag were analyzed. The sGFP fusion version of SaMscL (CΔ26) runs as two distinct final reaction products (FIG. 10B). If sGFP was the cause of mixed oligomerization, it was expected that the untagged protein would run as single band with a migration distance consistent with either a pentamer as suggested by the wild-type protein or the tetrameric form as suggested by the crystal structure of the deletion mutant. There was no evidence that sGFP alters the oligomeric forms of SaMscL(CΔ26). The untagged version of the protein, like fully cleaved SaMscL(CΔ26)-sGFP, migrates as two bands, consistent with a mixture of two oligomeric species (FIG. 11A) In addition, the intensity ratio of the lower to upper band is identical for both SaMscL(CΔ26) and SaMscL(CΔ26)-sGFP, indicating that the distribution between pentameric and tetrameric forms is approximately 1:1 and equivalent for both proteins (FIG. 12). However, there are variations between preparations which skew the ratio by as much as 10% in either direction.

A C-terminal Deletion of MtMscL does not Alter Oligomerization

Figure 13A:
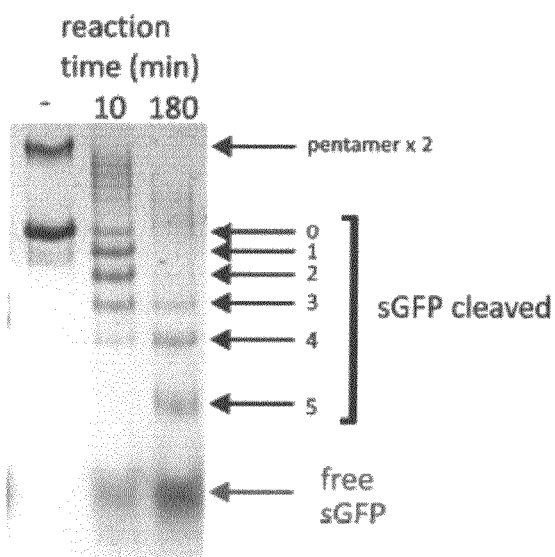
FIG. 13A is a BN-PAGE of a mass subtracted MtΔ49 MscL-sGFP complex according to embodiments of the present invention.
Figure 13B:
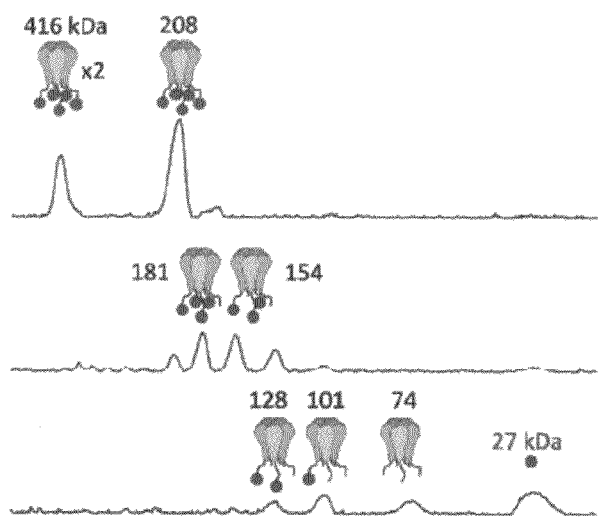
FIG. 13B is a comparison of densitometry traces of the BN-PAGE of FIG. 13A at 0, 10, and 180 minutes with schematics of the corresponding tagged/untagged complex according to embodiments of the present invention.

The mass subtraction results observed for SaMscL(CΔ26) immediately raised the question as to whether an identical truncation of MtMscL would cause it to behave in a similar manner. We created a truncation of MtMscL at position E102 (MtΔ49 MscL). This position is conserved between Mt, Sa and EcMscL, (FIG. 3B) and is the equivalent position of the SaMscL E95 truncation (SaMscL(CΔ26)). MtMscL(CΔ49) was fused to an sGFP mass partner, expressed, and purified in the detergent DDM. Like the wild-type MtMscL fusion, the purified MtMscL(CΔ49) fusion runs as a single band on an SDS gel and a single peak by size exclusion chromatography (not shown). FIG. 13A shows the results of an mass subtraction digestion. On a BN-PAGE gel, incomplete proteolytic cleavage of sGFP results in a ladder of six bands followed by free sGFP. Analysis of the densitometry shows that the ladder bands occur at a regular interval (FIG. 13B), and their positions are well described by a fit to the predicted masses of a family of reaction products resulting from the digestion of an initial pentamer. In addition, the untagged versions of Mt and MtMscL(CΔ49) both migrate as single bands by BN-PAGE, consistent with one oligomeric species (FIG. 11A). Taken together, these results indicate both wild-type and MtMscL (CΔ49) are pentamers and that the mixed oligomeric forms is not a general property of MscL C-terminal deletions.

The Wild-type EcMscL Channel Exists as a Mixture of Oligomers

The *E. coli* MscL homolog (EcMscL) is the most functionally characterized member of the MscL family. Although there is presently no crystal structure determined for EcMscL, electron microscopy and a study using tandem MscL subunits suggested that EcMscL may be hexameric, as reported by Blount et al., 1996, *EMBO J* 15:4798-4805; Saint et al., 1998, *J Biol Chem* 273:14667-14670, although more recent studies of tandem MscL fusions were interpreted to be pentameric, as reported by Sukharev et al., 1999, *J Membr Biol* 171:183-193; Folgering et al., 2005, *Protein Sci* 14:2947-2954. Cross-linking studies have suggested both hexameric and pentameric forms as reported by Chang et al., 1998, *Science* 282: 2220-2226; Sukharev et al., 1999, *J Membr Biol* 171:183-193; Folgering et al., 2005, *Protein Sci* 14:2947-2954; Yoshimura et al,. 2008, *Proc Natl Acad Sci USA* 105:4033-4038.

Figure 11B:
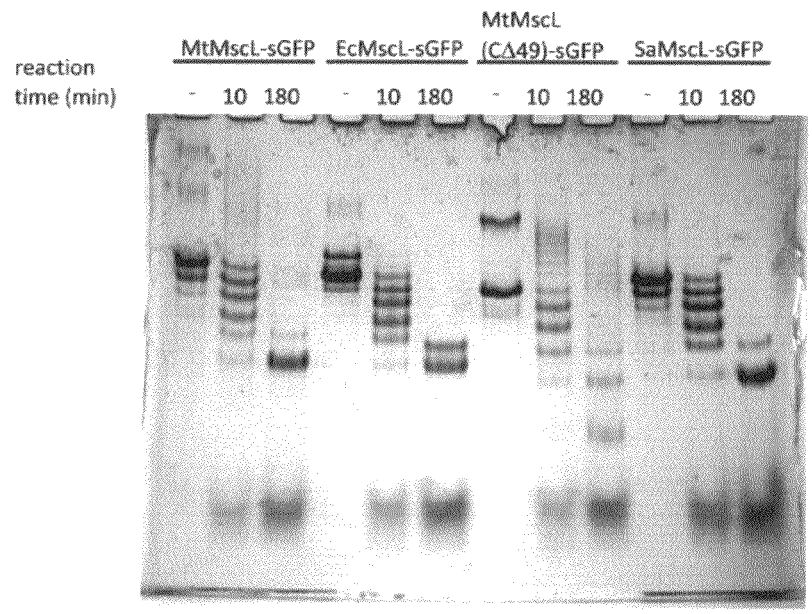
FIG. 11B is a BN-PAGE separation from mass subtraction of MtMscL-sGFP, EcMscL-sGFP, MtMscL(CΔ49)-sGFP, and SaMscL-sGFP tagged complexes according to embodiments of the present invention.
Figure 14A:
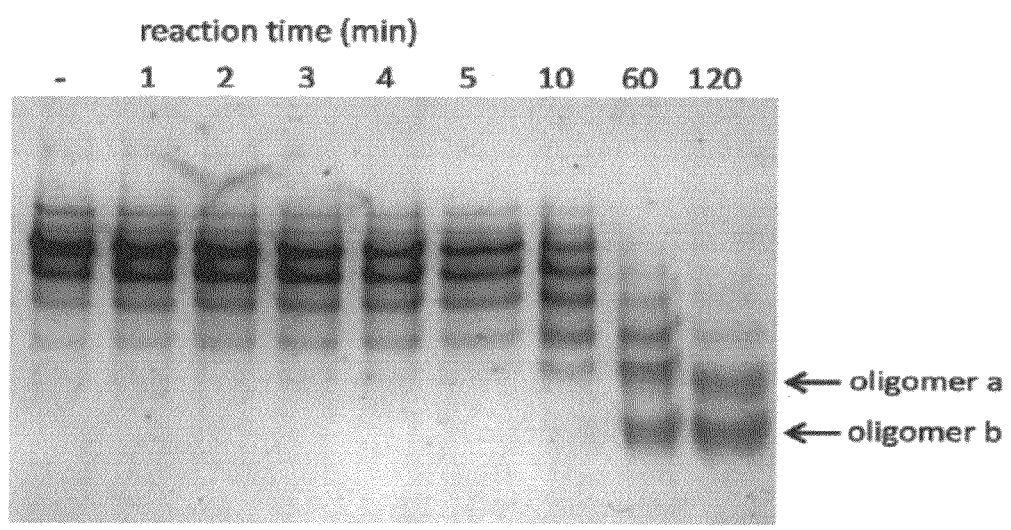
FIG. 14A is a BN-PAGE separation of a mass subtracted EcMscL-sGFP complex according to embodiments of the present invention.
Figure 14B:
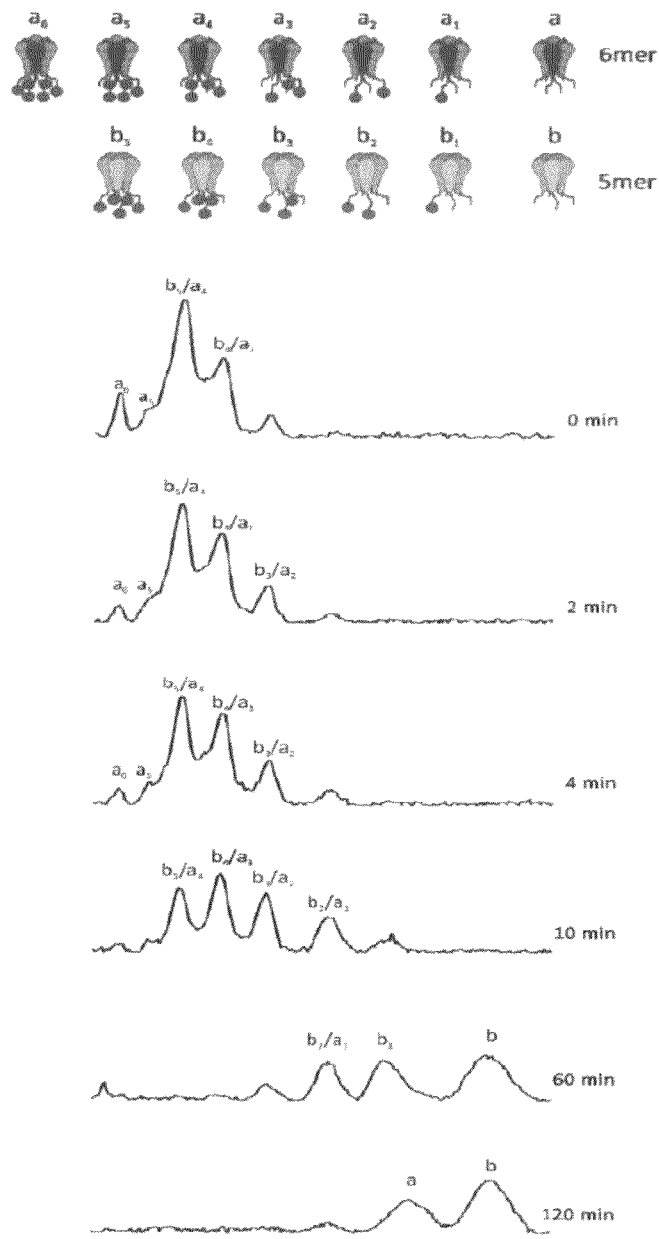
FIG. 14B is a comparison of densitometry traces of the BN-PAGE of FIG. 14A at 0, 2, 4, 10, 60, and 120 minutes with schematics of the corresponding tagged/untagged complex according to embodiments of the present invention.
Figure 14C:
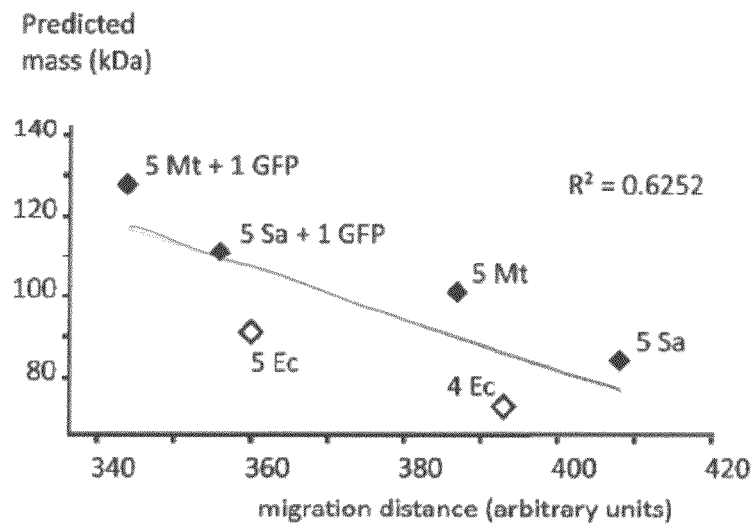
FIG. 14C is a graph showing a linear fit of predicted EcMscL pentameric and tetrameric masses together with the masses of the mass subtraction reaction products for SaMscL and MtMscL plotted against their measured migration distance according to embodiments of the present invention.
Figure 14D:
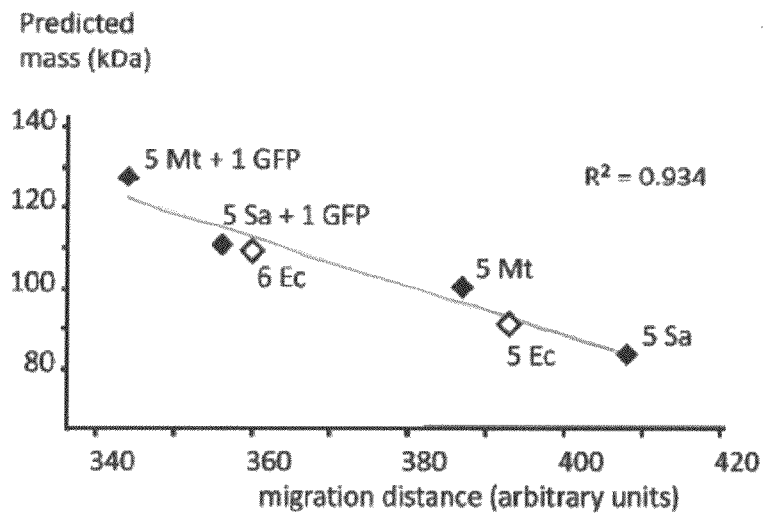
FIG. 14D is a graph showing a linear fit as in FIG. 14C, except with the predicted EcMscL hexameric and pentameric masses according to embodiments of the present invention.

Purified EcMscL-sGFP runs as a single band on an SDS gel and a single peak by size exclusion chromatography. FIGS. 14A and 14B show the results of a typical mass subtraction measurement. The family of reaction products is complex and qualitatively resembles the products observed for SaMscL (CΔ26). Like SaMscL(CΔ26), complete removal of the sGFP mass tag from EcMscL results in two bands of different apparent molecular weights, suggesting a mixture of oligomeric forms. However, unlike SaMscL(CΔ26), these bands migrate at distances inconsistent with a pentamer and tetramer, as the uppermost band has a migration distance above both full length pentameric Sa and MtMscL (FIG. 11B), suggesting the presence of a higher order oligomer. Densitometry reveals that the ladder of reaction products is formed by two different oligomeric species offset by the mass of a single MscL subunit. Given the earlier reports of EcMscL hexamers, the reaction ladder was studied to investigate if it is a mixture of hexamers and pentamers. A fully uncleaved hexamer would have a theoretical mass of 270 kDa while a fully uncleaved pentamer would have a mass of 225 kDa. Cleavage of a hexamer/pentamer mixture would create two ladders of reaction products whose masses are offset by only 9 kDa; however, this falls below the resolution limit of BN-PAGE which prevents a full count of the expected 13 reaction products (FIG. 6C). FIG. 14A shows the mass subtraction digestion time course. The corresponding densitometry clearly shows the presence of two unique high molecular weight bands and three unique low molecular weight bands flanking four bands of intermediate weight. The two lowermost bands correspond to fully cleaved products consistent with the two bands observed for EcMscL expressed without the sGFP mass tag (FIG. 11A) suggesting that wild-type EcMscL exists in at least two oligomeric forms. The intermediate bands are likely a combination of unresolvable products from the two oligomeric forms (FIG. 14B). The apparent molecular weights of the fully cleaved mass subtraction EcMscL reaction products were estimated by comparing their migration distances to the migration distances of the SaMscL and MtMscL mass subtraction reaction products using their assigned molecular weights as standards. The migration distances of mass subtraction reaction products can be empirically described by a log-linear relationship; however, over short migration distances the molecular weight of a reaction product can be estimated by a linear regression between products of known masses. By performing a linear fit of the migration distances of final SaMscL and MtMscL mass subtraction reaction products and comparing it to the migration distance of the final EcMscL mass subtraction products, an apparent molecular weight of 109-116 kDa and 92-95 kDa was estimated for the final products. These weights are in good agreement with the theoretical hexamer (110 kDa) and pentamer (91 kDa) masses (FIG. 6C). The migration distance of the assigned hexamer and pentamer bands have a corresponding $R^2$ value of 0.93 when fit to the Sa and Mt MscL migration curves (FIG. 14D), while an assigned pentamer and tetramer have an $R^2$ value of 0.63 (FIG. 14C). SEC-MALS measurements for the non-fusion EcMscL are consistent with a hexameric species (Table 1).

Molecular Biology

MscL-TEV linker-sGFP fusions were created using standard PIPE cloning and In-Fusion reactions. pET expression vectors carrying either Mt, Sa, or EcMscL were linearized by PCR to create a single PCR product opened between the last coding base pair at the 3' end of MscL and the adjacent stop codon. The 5' end of the PCR primers contained 18 base pairs of homology to an sGFP insert. All PCR products were treated with DpnI and gel purified. PIPE and In-Fusion reactions were performed as described in Klock et al., 2008, *Proteins* 71:982-994; Sleight et al., 2010, *Nucleic Acids Res* 38:2624-2636, the entire content of both of which is herein incorporated by reference.

Protein Expression

Expression plasmids were transformed into BL21-Gold (DE3) cells (Stratagene) or Rosetta (DE3) cells (EMD). A single colony was used to inoculate 20 ml of lysogeny broth-Miller (LB), as disclosed in Bertani, 2004, *J Bacteriol* 186: 595-600, the entire content of which is herein incorporated by reference; or Terrific Broth media with 1% glucose (TB glucose), and the culture was grown overnight at 37° C. with shaking at 225 rpm. One liter of LB or TB glucose media was inoculated with 20 ml of the overnight culture and shaken at 37° C. TB glucose cultures were grown until the absorbance at 600 nm reached 2.0. Expression was induced with 1 mM IPTG at 37° C. for 2 h. Cells were pelleted at 6,000g and stored at -20° C.

Protein Purification

Five grams of cell pellet were resuspended in 50 ml lysis buffer (50 mM Tris-HCl, 200 mM NaCl, 1% DDM, pH 8.0), passed four times through a microfluidizer, and centrifuged at 17,000 rpm (JA-17, Beckman) for 40 min at 4° C. The supernatant was gravity loaded onto a 2 ml Ni-NTA (Qiagen), washed with 1 column volume (CV) equilibration buffer (20 mM Tris-HCl, 150 mM NaCl, 10 mM imidazole, 0.05% DDM, pH 7.5) followed by 5 CV high salt buffer (20 mM Tris-HCl, 500 mM NaCl, 25 mM imidazole, 0.05% DDM, pH 7.5) 5 CV low imidazole wash buffer (20 mM Tris-HCl, 150 mM NaCl, 75 mM imidazole, 0.05% DDM, pH 7.5), and eluted in 3 CV elution buffer (20 mM Tris-HCl, 150 mM NaCl, 300 mM imidazole, 0.05% DDM, pH 7.5). The eluate was concentrated to ~10 mg/ml in 100 kDa cutoff concentrators (Amicon Ultra-4, Millipore) and loaded onto a Superdex 200 10/30 HR column (GE Healthcare) equilibrated in 20 mM Tris-HCl, 150 mM NaCl, 0.02% DDM, pH 7.5. The major peak fraction was collected and used directly for mass subtraction proteolytic digestion or SEC-MALS.

Mass Subtraction Proteolytic Digestion

Samples for mass subtraction experiments were suspended in reaction buffer (20 mM Tris pH7.5, 50 mM NaCl, 0.5 mM EDTA, 5 mM DTT) at 0.3 mg/ml. AcTEV protease (Invitrogen) was added at 1U/ug substrate and reactions were incubated at 34° C. Reactions were quenched at multiple time points by adding 10x stop solution (0.1 M Iodoacetamide, 0.1% Ponceau-S, and 50% Glycerol), and approximately 6 µg of substrate was loaded onto BN-PAGE gels for analysis. TEV protease is disclosed in Arnau et al., 2006, *Protein Expr Purif* 48:1-13, the entire contents of which is herein incorporated by reference.

Blue Native Page

BN-PAGE was performed as described with modifications in Wittig et al., 2006, *Nature protocols* 1:418-428; Ma et al., 2008, *Journal of applied crystallography* 41:1150-1160, the entire contents of all of these references are herein incorporate by reference. The anode buffer was 50 mM Bis-Tris pH 7.0. Two cathode buffers were used. Buffer A was 50 mM Tricine and 15 mM Bis-Tris pH 7.0, with 0.02% Coomassie Brilliant Blue G-250. Buffer B was the same as A but without Coomassie. Bio-Rad precast 4-15% Tris-HCl gradient gels were run with Buffer A at 150V for 1 hour followed by 4 hours at 150V using buffer B. In some cases Invitrogen Native Page 4-16% gradient gels were used. The anode buffer was constant throughout the run. All buffers were made at 4° C. and gels were run at 4° C. Gels were stained in 40% methanol/10% acetic acid with 0.2% Coomassie Brilliant Blue R and destained in 40% methanol/10% acetic acid followed by rehydration in water before imaging and densitometry analysis (Alpha Innotech). Traces were smoothed with a rolling ball algorithm implemented in AlphaEaseFC 6.0.0 for display purposes.

Detergents/Solubility

Detergents were purchased from Anatrace and are DM (n-decyl-β-d-maltopyranoside), DDM (n-dodecyl-β-d-maltopyranoside), FC12 (fos-choline-12), OG (n-octyl-β-d-glucopyranoside), LDAO (n-dodecyl-n,n-dimethylamine-n-oxide), C12E8 (octaethylene glycol monododecyl ether).

Detergent compatibility of mass subtraction measurements for SaMscL(CΔ26). SaMscL(CΔ26)-sGFP fusion protein was tested for protein solubility, BN PAGE migration, and TEV protease reactivity following purification in several detergents (FIGS. 3A-3B). SaMscL(CΔ26)-sGFP samples in DM, DDM, and C12E8 were soluble in TEV protease reaction conditions (34° C. for 15 minutes and 2 hours; ++), migrated through BN PAGE (++), and completely cleaved by TEV protease within 2 hours (++). The FC12 sample was soluble, compatible with BN PAGE, but resistant to TEV digestion (-). The OG sample was only partially soluble (+), compatible with BN PAGE, but completely resistant to TEV protease. The LDAO sample was soluble, displayed no BN PAGE migration, and was not tested for TEV protease reactivity (nd).

Size Exclusion Chromatography and Multi-Angle Light Scattering

Size exclusion chromatography coupled to multi-angle light scattering (SEC-MALS) was carried out using a Varian HPLC with three in-line detectors. Detectors were a Varian Prostar 345 UV detector followed by a DAWN HELEOS and an Optilab rEX (Wyatt Technologies). Samples were run over a Shodex KW803 column at 0.5 ml/min in 20 mM Tris pH 7.5, 150 mM NaCl, 0.02% DDM. Data was processed using the protein conjugate analysis implemented in Astra 5.3.4.16. UV extinction coefficients were calculated using Expasy Protparam, and detergent dn/dc values were obtained from Anatrace. The protein dn/dc value of 0.185 ml/g was used for all analysis. Protein molecular weight values are the average of three injections. Peak data was calculated at one half of the peak height. A single tryptophan was inserted into the N-terminal His tag of MtMscL and EcMscL to increase their UV extinction coefficients.

As shown and discussed throughout this disclosure, and for example, in FIGS. 7B, 9B, 10B, and 14A, the oligomeric states assigned by the mass/charge subtraction method of the present invention are consistent with the commonly used technique of size exclusion chromatography coupled to multi-angle light scattering (SEC-MALS) and existing crystal structures. More importantly, mass/charge subtraction provides for a more facile method for counting subunits of oligomeric complexes. Additionally, mass subtraction is able to identify the existence of oligomeric states not detected by SEC-MALS or crystallography.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A method of determining the number of protein subunits in a protein complex, the method, comprising:
    tagging a protein subunit of the protein complex to form a tagged protein subunit comprising a peptide tag and a protease cleavage site between the peptide tag and the protein subunit;
    expressing the tagged protein subunit in a cell culture or a cell-free extract to form a tagged protein complex comprising expressed tagged protein subunits;
    selectively digesting the tagged protein complex at at least two different time points with a protease to form an analyte mixture comprising undigested protein complex, intermediate reaction products, and/or digested protein complex;
    separating the undigested protein complex, the intermediate reaction products, and/or the digested complex of the analyte mixture; and
    determining the number of protein subunits in the protein complex by analyzing the presence of, or the progressive loss of, the peptide tag in each of the undigested protein complex, the intermediate reaction products, and/or the digested protein complex.

2. The method of claim 1, wherein separating the analyte mixture comprises a technique selected from the group consisting of native polyacrylamide gel electrophoresis (PAGE), isoelectric focusing (IEF) electrophoresis, and combinations thereof.

3. The method of claim 1, wherein separating the analyte mixture comprises clear native PAGE or blue native PAGE.

4. The method of claim 1, wherein separating the analyte mixture comprises native PAGE, the method further comprising analyzing the native PAGE by a technique selected from the group consisting of Coomassie stain, Western blot, in-gel fluorescence, in-gel luminescence, and combinations thereof.

5. The method of claim 1, wherein separating the mixture comprises IEF electrophoresis using an IEF gel or an IEF strip.

6. The method of claim 1, wherein the protein complex comprises a membrane protein complex or a soluble protein complex.

7. The method of claim 1, wherein the protein complex comprises a homo-oligomeric complex or a hetero-oligomeric complex.

8. The method of claim 1, wherein the protein complex comprises a homo-oligomeric complex or a hetero-oligomeric complex, and the protein complex is a mixed oligomeric species.

9. The method of claim 1, wherein the peptide tag comprises a mass tag or a charge tag.

10. The method of claim 1, wherein the peptide tag comprises a mass tag having a mass of at least 5 kilodaltons.

11. The method of claim 1, wherein the peptide tag comprises fluorescent protein tags, glutathione s-transferase (GST) tags, maltose binding protein (MBP), chitin binding protein, cellulose-binding protein, calmodulin binding peptide, streptavidin binding peptide (SBP), poly-arginine, poly-histidine, FLAG (DYKDDDDK), 3x FLAG, streptavidin (strep)-tag II, c-myc, RNaseA S-peptide (S-tag), natural histidine affinity tag (HAT), alkaline phosphatase (ALP), β-D-galactosidase, β-D-glucose oxidase, luciferase, peroxidase, and xanthine oxidase.

12. The method of claim 1, wherein the protease cleavage site is cleavable by a protease selected from the group consisting of tobacco etch virus (TEV), human rhino virus (HRV) 3C, thrombin, Factor Xa, and enterokinase.

13. The method of claim 1, wherein the culture is a cell culture, and the method further comprises lysing the cells of the culture to form a cell lysate comprising the expressed tagged protein subunit.

14. The method of claim 1, wherein the method further comprises isolating the tagged protein complex from the culture to form an isolated tagged protein complex.

15. The method of claim 1, wherein the peptide tag comprises a charge tag having a pI that is different from the pI of the protein subunit.

16. The method of claim 1, wherein the peptide tag comprises a mass tag having a mass that is different from the mass of the protein subunit.

17. The method of claim 1, wherein the at least two different time points comprise a zero time point, an endpoint, and a time point in between the zero time point and the endpoint.

* * * * *